(12) United States Patent
Yano et al.

(10) Patent No.: US 8,247,504 B2
(45) Date of Patent: *Aug. 21, 2012

(54) CATALYST COMPONENT, CATALYST FOR OLEFIN POLYMERIZATION, AND PROCESS FOR PRODUCING OLEFIN POLYMER USING CATALYST

(75) Inventors: Takefumi Yano, Chigasaki (JP); Motoki Hosaka, Chigasaki (JP); Maki Sato, Chigasaki (JP); Kohei Kimura, Chigasaki (JP)

(73) Assignee: Toho Titanium, Co.,. Ltd., Chiagasaki-ski (JP)

( * ) Notice: Subject to any disclaimer, the term of this patent is extended or adjusted under 35 U.S.C. 154(b) by 391 days.

This patent is subject to a terminal disclaimer.

(21) Appl. No.: 11/997,924

(22) PCT Filed: Aug. 4, 2006

(86) PCT No.: PCT/JP2006/315895
§ 371 (c)(1),
(2), (4) Date: Apr. 5, 2010

(87) PCT Pub. No.: WO2007/018280
PCT Pub. Date: Feb. 15, 2007

(65) Prior Publication Data
US 2010/0190938 A1    Jul. 29, 2010

(30) Foreign Application Priority Data

Aug. 8, 2005   (JP) ................ 2005-229418
Aug. 8, 2005   (JP) ................ 2005-229420

(51) Int. Cl.
*C08F 4/44* (2006.01)
*C07F 7/02* (2006.01)
*B01J 31/00* (2006.01)
*B01J 37/00* (2006.01)
*C08K 3/34* (2006.01)

(52) U.S. Cl. .............. 526/125.3; 526/128; 526/160; 556/410; 502/116; 502/152; 524/445

(58) Field of Classification Search .......... 526/125.3, 526/128, 160; 556/410; 502/116, 152; 524/445
See application file for complete search history.

(56) References Cited

U.S. PATENT DOCUMENTS
2004/0097366 A1*   5/2004   Sato et al. ............... 502/152
(Continued)

FOREIGN PATENT DOCUMENTS
JP    57 63310    4/1982
(Continued)

OTHER PUBLICATIONS
U.S. Appl. No. 13/289,728, filed Nov. 4, 2011, Hosaka, et al.
(Continued)

*Primary Examiner* — William Cheung
(74) *Attorney, Agent, or Firm* — Oblon, Spivak, McClelland, Maier & Neustadt, L.L.P.

(57) ABSTRACT

A polymer having high catalyst activity, excellent hydrogen response, high stereoregularity and high yield can be obtained by polymerizing olefins in the presence of a catalyst for olefin polymerization comprising (A) a solid catalyst component containing magnesium, titanium, a halogen, and an electron donor compound, (B) an organoaluminum compound shown by the formula $R^6_p AlQ_{3-p}(R^1R^2N)_m$, and (C) an aminosilane compound shown by the formula $(R^3HN)_n R^4_p Si(OR^5)_q$.

20 Claims, 1 Drawing Sheet

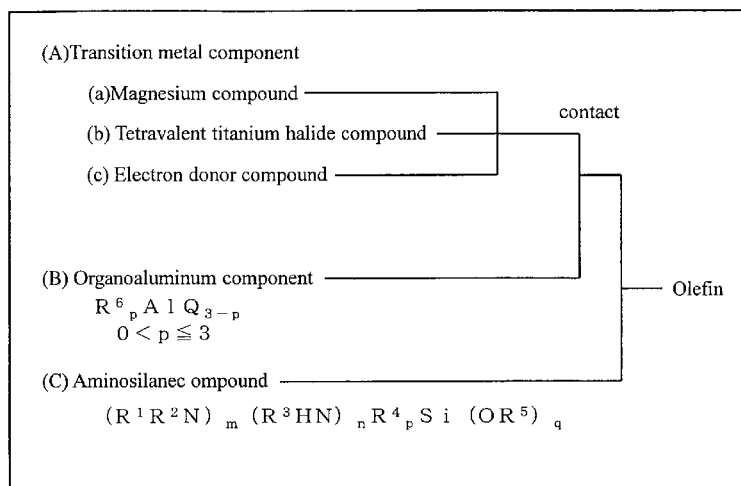

U.S. PATENT DOCUMENTS

2005/0032991 A1 * 2/2005 Chosa et al. .............. 526/125.3

FOREIGN PATENT DOCUMENTS

| | | |
|---|---|---|
| JP | 57 63311 | 4/1982 |
| JP | 63 3010 | 1/1988 |
| JP | 1 315406 | 12/1989 |
| JP | 7 109304 | 4/1995 |
| JP | 2005 48045 | 2/2005 |
| JP | 2006 63281 | 3/2006 |
| JP | 2006 63282 | 3/2006 |
| WO | 2004 016662 | 2/2004 |

OTHER PUBLICATIONS

U.S. Appl. No. 13/120,027, filed Mar. 21, 2011, Hosaka.

* cited by examiner (A) Transition metal component
    (a) Magnesium compound
    (b) Tetravalent titanium halide compound
    (c) Electron donor compound contact (B) Organoaluminum component
$$R^6{}_p Al Q_{3-p}$$
$$0 < p \leq 3$$

(C) Aminosilane ompound
$$(R^1R^2N)_m (R^3HN)_n R^4{}_p Si (OR^5)_q$$

Olefin

CATALYST COMPONENT, CATALYST FOR OLEFIN POLYMERIZATION, AND PROCESS FOR PRODUCING OLEFIN POLYMER USING CATALYST

This application is a 371 of PCT/JP2006/315895, filed Aug. 4, 2006.

TECHNICAL FIELD

The present invention relates to a catalyst component and a catalyst for polymerization of olefins capable of maintaining high stereoregularity and yield of the polymer and capable of producing olefin polymers having a high melt flow rate with a given amount of hydrogen (excellent hydrogen response), and to a process for producing olefin polymers using the catalyst component or the catalyst.

BACKGROUND ART

A solid catalyst component containing magnesium, titanium, an electron donor compound, and a halogen as essential components used for polymerization of olefins such as propylene has been known in the art. A large number of methods for polymerizing or copolymerizing olefins in the presence of a catalyst for olefin polymerization comprising the above solid catalyst component, an organoaluminum compound, and an organosilicon compound have been proposed. For example, Patent Document 1 (JP-A-57-63310) and Patent Document 2 (JP-A-57-63311) propose a method for polymerizing olefins with three or more carbon atoms, in which a catalyst comprising a combination of a magnesium compound, a titanium compound, and an organosilicon compound having an Si—O—C bond is used. However, because the method is not necessarily satisfactory for producing highly stereoregular polymers in a high yield, improvement of these methods has been desired.

Patent Document 3 (JP-A-63-3010) proposes a catalyst and a method for polymerizing propylene. The catalyst comprises a solid catalyst component, obtained by processing a powder produced from a dialkoxy magnesium, an aromatic dicarboxylic acid diester, an aromatic hydrocarbon, and a titanium halide with heat, an organoaluminum compound, and an organosilicon compound.

Patent Document 4 (JP-A-1-315406) proposes another catalyst for propylene polymerization and a method for polymerizing propylene in the presence of this catalyst. The catalyst for propylene polymerization comprises a solid catalyst component prepared by causing a suspension liquid containing diethoxymagnesium and an alkylbenzene to come in contact with titanium tetrachloride, reacting the suspension liquid with phthalic acid chloride, and causing the resulting solid product to come in contact with titanium tetrachloride in the presence of an alkylbenzene, an organoaluminum compound, and an organosilicon compound.

All of the above-described technologies have attained certain results in improving catalytic activity to the extent of permitting dispensing with an ash-removal step for removing catalyst residues such as chlorine and titanium from formed polymers, improving the yield of stereoregular polymers, and improving durability of catalytic activity during polymerization. However, there is a demand for continued improvement of such a catalyst.

The polymers produced using these catalysts are used in a variety of applications including formed products such as vehicles and household electric appliances, containers, and films. These products are manufactured by melting polymer powders produced by polymerization and, after palletizing, forming the polymer using various molds. In manufacturing formed products, particularly large products by injection molding, melted polymers are sometimes required to have a high fluidity (melt flow rate: MRF). In particular, for the purpose of cost reduction in the manufacture of a highly functional block copolymer to be used as a vehicle material, in a method of producing a copolymer in an amount just required for obtaining an olefin-based thermoplastic elastomer (hereinafter referred to as "TPO") in a copolymerization reactor, and obtaining the TPO directly in the polymerization reactor without adding a separately produced copolymer, that is, in so-called "manufacture of a reactor-made TPO by direct polymerization", a melt flow rate of 200 or more is demanded in a homopolymerization stage in order to produce a finished product with a high melt flow rate and to ensure ease of injection molding. For this reason, many studies for increasing the melt flow rate of polymers have been undertaken.

The melt flow rate greatly depends on the molecular weight of the polymers. In the industry, hydrogen is generally added as a molecular weight regulator for polymers during polymerization of propylene. In this instance, a large quantity of hydrogen is usually added to produce low molecular weight polymers having a high melt flow rate. However, the quantity of hydrogen which can be added is limited because pressure resistance of the reactor is limited for the sake of safety. In order to add a larger amount of hydrogen in vapor phase polymerization, the partial pressure of monomers to be polymerized has to be decreased, resulting in a decrease in productivity. The use of a large amount of hydrogen also brings about a problem of cost. As a method for solving this problem, Patent Document 5 (WO 2004-16662) proposes a method of producing a polymer having a high melt flow rate by using a compound shown by the formula $Si(OR^1)_3(NR^2R^3)$ as a catalyst component for polymerization of olefins.

However, because these methods are not necessarily satisfactory for basically solving the above problems of TPO production by direct polymerization, improvement of these methods has been desired.

(Patent Document 1) JP-A-57-63310 (Claims)
(Patent Document 2) JP-A-57-63311 (Claims)
(Patent Document 3) JP-A-63-3010 (Claims)
(Patent Document 4) JP-A-1-315406 (Claims)
(Patent Document 5) WO 2004-16662 (Claims)

Therefore, an object of the present invention is to provide a catalyst component and a catalyst for polymerization of olefins capable of excellently maintaining stereoregularity and yield of a polymer and capable of producing olefin polymers having a high melt flow rate with a given amount of hydrogen (excellent hydrogen response), and a process for producing an olefin polymer using the catalyst component or the catalyst.

DISCLOSURE OF THE INVENTION

In view of this situation, the inventors have conducted extensive studies. As a result, the inventors have found that a catalyst for olefin polymerization containing an aminosilane compound with a specific structure as an active component, or a catalyst formed from a solid catalyst component containing magnesium, titanium, a halogen, and an electron donor compound, an organoaluminum compound, and an aminosilane compound having a specific structure is suitable as a catalyst for polymerizing olefins as compared with general catalysts, and that the aminosilane compound has not been known heretofore to be usable as an electron donor compound (an internal donor) of a solid catalyst component or an electron donor compound of a catalyst (an external donor). These findings have led to the completion of the present invention.

Specifically, the present invention provides a catalyst component for olefin polymerization shown by the following formula (1),

$$(R^1R^2N)_m(R^3HN)_nR^4_p\mathrm{Si}(OR^5)_q \qquad (1)$$

wherein m is an integer of 0, 1, or 2, n and q are integers of 1 to 3, and p is an integer of 0, 1, or 2, wherein m+n+p+q=4, when m=0, q=1 and p=3-n; $R^1$, $R^2$, and $R^3$ individually represent a linear or branched alkyl group having 1 to 20 carbon atoms, a cycloalkyl group or a derivative thereof, a vinyl group, an allyl group, or an aralkyl group, each of which may contain a hetero atom, wherein $R^1$ and $R^2$ may bond to form a ring; $R^4$ individually represents a linear or branched alkyl group having 1 to 20 carbon atoms, a cycloalkyl group or a derivative thereof, a vinyl group, an allyl group, or an aralkyl group, each of which may contain a hetero atom, and, when m=0, n=1, and q=1, two $R^4$s may bond to form a ring; and $R^5$ individually represents a linear or branched alkyl group having 1 to 12 carbon atoms, a cycloalkyl group or a derivative thereof, a vinyl group, an allyl group, or an aralkyl group, each of which may contain a hetero atom.

The present invention also provides a catalyst for olefin polymerization comprising the above-mentioned catalyst component for olefin polymerization.

The present invention further provides a catalyst for polymerization of olefins comprising (A) a solid catalyst component containing magnesium, titanium, a halogen, and an electron donor compound, (B) an organoaluminum compound of the following formula (2),

$$R^6_p\mathrm{AlQ}_{3-p} \qquad (2)$$

wherein $R^6$ represents an alkyl group having 1 to 4 carbon atoms, Q represents a hydrogen atom or a halogen atom, and p represents a real number satisfying the formula $0 \leq p \leq 3$, and (C) the above-mentioned catalyst component for olefin polymerization, Moreover, the present invention provides a process for producing an olefin polymer, wherein polymerization of the olefin is carried out in the presence of the catalyst for olefin polymerization.

BRIEF DESCRIPTION OF THE DRAWING

FIG. 1 is a flowchart showing a process for preparing the catalyst component and polymerization catalyst of the present invention.

BEST MODE FOR CARRYING OUT THE INVENTION

The catalyst component for olefin polymerization of the present invention is the aminosilane compound shown by the above-mentioned formula (1). The catalyst for olefin polymerization of the present invention contains the aminosilane compound shown by the above-mentioned formula (1) as an effective component. Specifically, the aminosilane compound can be used as an electron donor (internal donor) compound of the solid catalyst component, which is an essential component of the olefin polymerization catalyst, and an electron donor compound (external donor) of the olefin polymerization catalyst.

The aminosilane compound shown by the above formula (1) is a compound having a nitrogen atom directly bonded to a silicon atom. As examples of the hetero atom of the formula (1), an oxygen atom, a nitrogen atom, a sulfur atom, and a silicon atom can be given. As examples of the derivative of the cycloalkyl group, a cycloalkyl group having a substituent such as an alkyl-substituted cyclopentyl group, an alkyl-substituted cyclohexyl group, and an alkyl-substituted cycloheptyl group can be given.

$R^1$, $R^2$, and $R^3$ in the formula (1) are preferably linear or branched alkyl groups having 1 to 10 carbon atoms or cycloalkyl groups having 5 to 8 carbon atoms, with particularly preferable groups being linear or branched alkyl groups having 1 to 8 carbon atoms or cycloalkyl groups having 5 to 8 carbon atoms. As the $R^1R^2N$ group produced by ring-formation of $R^1$ and $R^2$, a perhydroquinolino group and a perhydroisoquinolino group are preferable. $R^4$ is preferably a linear or branched alkyl group having 1 to 10 carbon atoms or a cycloalkyl group having 5 to 8 carbon atoms, with particularly preferable groups being a linear or branched alkyl group having 1 to 8 carbon atoms or a cycloalkyl group having 5 to 8 carbon atoms. $R^5$ is preferably a linear or branched alkyl group having 1 to 6 carbon atoms, with a particularly preferable group being a linear or branched alkyl group having 1 to 4 carbon atoms.

The compound groups shown by the formula (1) particularly include a group wherein m=n=p=q=1 (a first compound group), a group wherein m=0, n=1, p=2, and q=1 (a second compound group), a group wherein m=0, n=3, p=0, and q=1 (a third compound group), a group wherein m=1, n=1, p=0, q=2 (a fourth compound group), a group wherein m=1, n=2, p=0, and q=1 (a fifth compound group), a group wherein m=2, n=1, p=0, and q=1 (a sixth compound group), a group wherein m=1, n=2, p=0, and q=1 (a seventh compound group), a group wherein m=0, n=1, p=1, and q=2 (an eighth compound group), a group wherein m=0, n=2, p=1, and q=1 (a ninth compound group), a group wherein m=0, n=1, p=0, and q=3 (a tenth compound group), and a group wherein m=0, n=2, p=0, and q=2 (an eleventh compound group). Among these, the first to ninth compound groups are preferable.

As examples of the first compound group, an alkyl(dialkylamino)(alkylamino)alkoxysilane, a cycloalkyl(dialkylamino)(alkylamino)alkoxysilane, a vinyl(dialkylamino)(alkylamino)alkoxysilane, an allyl(dialkylamino)(alkylamino)alkoxysilane, an aralkyl(dialkylamino)(alkylamino)alkoxysilane, and a dialkyl(alkylamino)alkoxysilane can be given. Of these, an alkyl(dialkylamino)(alkylamino)alkoxysilane is preferable.

In the first compound group, $R^1$, $R^2$, and $R^3$ in the formula (1) are preferably linear or branched alkyl groups having 1 to 8 carbon atoms or cycloalkyl groups having 5 to 8 carbon atoms. As the $R^1R^2N$ group produced by ring-formation of $R^1$ and $R^2$, a perhydroquinolino group and a perhydroisoquinolino group are preferable. $R^4$ is preferably a linear or branched alkyl group having 1 to 8 carbon atoms or a cycloalkyl group having 5 to 8 carbon atoms. $R^5$ is preferably a linear or branched alkyl group having 1 to 4 carbon atoms, particularly a methyl group, an ethyl group, or a propyl group.

As specific preferable examples of the compound in the first compound group, (perhydroisoquinolino)(methylamino)ethylmethoxysilane, (ethylamino)(diethylamino)(methoxy)vinylsilane, (ethylamino)(dimethylamino)(ethoxy)cyclopentylsilane, (ethylamino)(diethylamino)(ethoxy)isopropylsilane, (ethylamino)(dimethylamino)(methoxy)thexylsilane, (ethylamino)(dimethylamino)(ethoxy)vinylsilane, and (ethylamino)(diethylamino)(ethoxy)-p-methoxyphenylsilane can be given.

As examples of the second group compound, a dialkyl(cycloalkylamino)alkoxysilane, an alkylcycloalkyl(alkylamino)alkoxysilane, an alkylcycloalkyl(cycloalkylamino)

alkoxysilane, a dicycloalkyl(alkylamino)alkoxysilane, a dicycloalkyl(cycloalkylamino)alkoxysilane, a divinyl(alkylamino)alkoxysilane, an alkylallyl(alkylamino)alkoxysilane, an alkylallyl(cycloalkylamino)alkoxysilane, a cycloalkylallyl(alkylamino)alkoxysilane, a cycloalkylallyl(cycloalkylamino)alkoxysilane, an diallyl(alkylamino)alkoxysilane, a diallyl(cycloalkylamino)alkoxysilane, an alkylaralkyl(alkylamino)alkoxysilane, an alkylaralkyl(cycloalkylamino) alkoxysilane, a cycloalkylaralkyl(alkylamino)alkoxysilane, a cycloalkylaralkyl(cycloalkylamino)alkoxysilane, a diaralkyl (alkylamino)alkoxysilane, a diaralkyl(cycloalkylamino) alkoxysilane, a dialkenyl(alkylamino)alkoxysilane, a dicycloalkenyl(alkylamino)alkoxysilane, an alkylalkenyl (alkylamino)alkoxysilane, a cycloalkylalkenyl(alkylamino) alkoxysilane, an alkylcycloalkenyl(alkylamino) alkoxysilane, and a cycloalkylcycloalkenyl(alkylamino) alkoxysilane can be given. Of these, a dialkyl (cycloalkylamino)alkoxysilane, an alkylcycloalkyl (alkylamino)alkoxysilane, an alkylcycloalkyl (cycloalkylamino)alkoxysilane, a dicycloalkyl(alkylamino) alkoxysilane, and a dicycloalkyl(cycloalkylamino) alkoxysilane are preferable.

As examples of the compound formed by ring-formation of two $R^4$s of the formula (1), a 1-(alkyamino)-1-(alkoxy)silacycloalkane, a 1-(cycloalkyamino)-1-(alkoxy)silacycloalkane, a 1-(alkyamino)-1-(alkoxy)monoalkyl-substituted silacycloalkane, a 1-(alkyamino)-1-(alkoxy)dialkyl-substituted silacycloalkane, a 1-(cycloalkyamino)-1-(alkoxy) monoalkyl-substituted silacycloalkane, and a 1-(cycloalkyamino)-1-(alkoxy)dialkyl-substituted silacycloalkane can be given.

In the second compound group, $R^3$ in the formula (1) is preferably a linear or branched alkyl group having 1 to 8 carbon atoms or a cycloalkyl group having 5 to 8 carbon atoms. $R^4$ is preferably a substituted or unsubstituted, linear or branched alkyl group having 1 to 12 carbon atoms or a substituted or unsubstituted cycloalkyl group having 5 to 8 carbon atoms. $R^5$ is preferably a linear or branched alkyl group having 1 to 4 carbon atoms, particularly a methyl group, an ethyl group, or an n-propyl group.

As specific preferable examples of the compound of the second compound group, dicyclopentyl(methylamino)methoxysilane, dicyclopentyl(ethylamino)methoxysilane, diisopropyl(methylamino)ethoxysilane, cyclohexylmethyl(ethylamino)ethoxysilane, cyclohexylmethyl(methylamino) methoxysilane, t-butylethyl(methylamino)methoxysilane, t-butylmethyl(ethylamino)ethoxysilane, t-butylmethyl(ethylamino)methoxysilane, dicyclohexyl(ethylamino)methoxysilane, di-t-butyl(methylamino)methoxysilane, diisopropyl (n-propylamino)methoxysilane, phenylmethyl (methylamino)methoxysilane, diisopropyl(ethylamino)n-propoxysilane, p-methoxyphenylmethyl(ethylamino) ethoxysilane, thexylmethyl(ethylamino)methoxysilane, didecahydronaphthyl(ethylamino)methoxysilane, tris(n-decylamino)methoxysilane, (ethylamino)(methoxy)-2,5-dimethylsilacyclopentane, (ethylamino)(methoxy)-2,6-dimethylsilacyclohexane, benzylethyl(ethylamino)ethoxysilane, and phenylvinyl(ethylamino)methoxysilane can be given.

As examples of the compound of the third compound group, a tri(alkylamino)alkoxysilane, a tri(cycloalkylamino) alkoxysilane, a di(alkylamino)(cycloalkylamino)alkoxysilane, and (alkylamino)di(cycloalkylamino)alkoxysilane can be given. Of these, a tri(alkylamino)alkoxysilane and a tri (cycloalkylamino)alkoxysilane are preferable.

In the third compound group, $R^3$ in the formula (1) is preferably a linear or branched alkyl group having 1 to 10, particularly 1 to 6, carbon atoms, or a cycloalkyl group having 5 to 8 carbon atoms. $R^5$ is preferably a linear or branched alkyl group having 1 to 4 carbon atoms, particularly a methyl group, an ethyl group, or a n-propyl group.

As the specific preferable examples of the compound of the third compound group, tris(ethylamino)methoxysilane, tris (isopropylamino)ethoxysilane, tris(cyclopentylamino)methoxysilane, tris(cyclohexylamino)methoxysilane, bis(t-butylamino)(methylamino)methoxysilane, (t-butylamino) (methylamino)(ethylamino)methoxysilane, bis (cyclohexylamino)(ethylamino)ethoxysilane, bis (isobutylamino)(methylamino)propoxysilane, tris(n-decylamino)methoxysilane, tris(ethylamino)t-butoxysilane, and tris(ethylamino)cyclohexoxysilane can be given.

As examples of the compound of the fourth compound group, a (dialkylamino)(alkylamino)dialkoxysilane, an (alkylcycloalkylamino)(alkylamino)dialkoxysilane, and a (dicycloalkylamino)(alkylamino)dialkoxysilane can be given.

In the fourth compound group, $R^1$, $R^2$, and $R^3$ in the formula (1) are preferably linear or branched alkyl groups having 1 to 8, particularly 1 to 6, carbon atoms, or cycloalkyl groups having 5 to 8 carbon atoms. As the $R^1R^2N$ group produced by ring-formation of $R^1$ and $R^2$, a perhydroquinolino group and a perhydroisoquinolino group are preferable. $R^5$ is preferably a linear or branched alkyl group having 1 to 4 carbon atoms, particularly a methyl group, an ethyl group, or an n-propyl group.

As specific preferable examples of the compound of the fourth compound group, (di-t-butylamino)(ethylamino)diethoxysilane, (cyclopentylamino)(diphenylamino) dimethoxysilane, and (benzylamino)(diisopropylamino)diethoxysilane can be given.

As examples of the compound of the fifth compound group, a (dialkylamino)di(alkylamino)alkoxysilane, an (alkylcycloalkylamino)di(alkylamino)alkoxysilane, and a (dicycloalkylamino)di(alkylamino)alkoxysilane can be given. Of these, a (dialkylamino)di(alkylamino)alkoxysilane is preferable.

In the fifth compound group, $R^1$, $R^2$, and $R^3$ in the formula (1) are preferably linear or branched alkyl groups having 1 to 8, particularly 1 to 6, carbon atoms, or cycloalkyl groups having 5 to 8 carbon atoms. As the $R^1R^2N$ group produced by ring-formation of $R^1$ and $R^2$, a perhydroquinolino group and a perhydroisoquinolino group are preferable. $R^5$ is preferably a linear or branched alkyl group having 1 to 4 carbon atoms, particularly a methyl group, an ethyl group, or an n-propyl group.

As specific preferable examples of the compound of the fifth compound group, (di-t-butylamino)(t-butylamino) (ethylamino)methoxysilane and bis(ethylamino)(diethylamino)ethoxysilane can be given.

As examples of the compound of the sixth compound group, a (dialkylamino)(alkylamino)alkoxysilane, a di(alkylcycloalkylamino)(alkylamino)alkoxysilane, and a di(dicycloalkylamino)(alkylamino)alkoxysilane can be given.

In the sixth compound group, $R^1$, $R^2$, and $R^3$ in the formula (1) are preferably linear or branched alkyl groups having 1 to 8, particularly 1 to 6, carbon atoms, or cycloalkyl groups having 5 to 8 carbon atoms. As the $R^1R^2N$ group produced by ring-formation of $R^1$ and $R^2$, a perhydroquinolino group and a perhydroisoquinolino group are preferable. $R^5$ is preferably a linear or branched alkyl group having 1 to 4 carbon atoms, particularly a methyl group, an ethyl group, or an n-propyl group.

As specific preferable examples of the compound of the sixth compound group, bis(perhydroisoquinolino)(methylamino)methoxysilane, bis(perhydroisoquinolino)(ethylamino)methoxysilane, bis(diethylamino)(ethylamino)methoxysilane, and bis(diethylamino)(ethylamino)n-butoxysilane can be given.

As examples of the compound of the seventh compound group, a (dialkylamino)di(alkylamino)alkoxysilane, an (alkylcycloalkylamino)(alkylamino)(cycloalkylamino) alkoxysilane, and a (dialkylamino)di(cycloalkylamino) alkoxysilane can be given.

In the seventh compound group, $R^1$, $R^2$, and $R^3$ in the formula (1) are preferably linear or branched alkyl groups having 1 to 8, particularly 1 to 6, carbon atoms, or cycloalkyl groups having 5 to 8 carbon atoms. As the $R^1R^2N$ group produced by ring-formation of $R^1$ and $R^2$, a perhydroquinolino group and a perhydroisoquinolino group are preferable. $R^5$ is preferably a linear or branched alkyl group having 1 to 4 carbon atoms, particularly a methyl group, an ethyl group, or an n-propyl group.

As examples of the compound of the seventh compound group, bis(ethylamino)(diphenylamino)ethoxysilane and the like can be given.

As examples of the compound of the eighth compound group, an alkyl(alkylamino)dialkoxysilane and a cycloalkyl(alkylamino)dialkoxysilane can be given. As specific examples of the compound of the eighth compound group, t-butyl(ethylamino)diethoxysilane, cyclohexyl(ethylamino) dimethoxysilane, ethyl(t-butylamino)dimethoxysilane, and ethyl(t-butylamino)diethoxysilane can be given. As examples of the compound of the ninth compound group, an alkyldi(alkylamino)alkoxysilane, a cycloalkyldi(alkylamino)alkoxysilane, an alkyldi(cycloalkylamino)alkoxysilane, an alkyl(alkylamino)(cycloalkylamino)alkoxysilane, an allyldi(alkylamino)alkoxysilane, and an aralkyldi(alkylamino) alkoxysilane can be given. As specific examples of the compound of the ninth compound group, bis(ethylamino)sec-butylmethoxysilane and bis(ethylamino)cyclopentylmethoxysilane can be given. As examples of the compound of the tenth compound group, an (alkylamino)trialkoxysilane and a (cycloalkylamino)trialkoxysilane can be given. As examples of the compound of the eleventh compound group, a di(alkylamino)dialkoxysilane, an (alkylamino)(cycloalkylamino)dialkoxysilane, and a di(cycloalkylamino)dialkoxysilane can be given.

These compounds can be synthesized by a general synthesis method such as a chlorine exchange method, a method using an organolithium compound, or a method using a Grignard reagent, or by combination of these methods. It is also possible to produce these compounds by synthesizing a synthetic intermediate such as tetrakis(alkylamino)silane and reacting the synthetic intermediate with various types of alcohols or phenols under specific conditions.

In addition to the above-described aminosilane compound of the formula (1), the catalyst for olefin polymerization of the present invention may include a solid catalyst component (A) (hereinafter may be simply referred to as "component (A)") and an organoaluminum compound. A general solid catalyst component (A) and organoaluminum compound may be used.

Among the components of the catalyst for olefin polymerization of the present invention, the component (A), which comprises magnesium, titanium, a halogen, and an electron donor compound, can be obtained by causing (a) a magnesium compound, (b) a tetravalent titanium halogen compound, and (c) an electron donor compound to come in contact with each other.

As examples of the magnesium compound (hereinafter simply referred to as "component (a)" from time to time), a magnesium dihalide, a dialkylmagnesium, an alkylmagnesium halide, a dialkoxymagnesium, a diaryloxymagnesium, an alkoxymagnesium halide, and a fatty acid magnesium can be given. Among these magnesium compounds, a magnesium dihalide, a mixture of magnesium dihalide and dialkoxy magnesium, and a dialkoxy magnesium are preferable, and a dialkoxy magnesium is particularly preferable. As specific examples, dimethoxy magnesium, diethoxy magnesium, dipropoxy magnesium, dibutoxy magnesium, ethoxymethoxy magnesium, ethoxypropoxy magnesium, and butoxyethoxy magnesium can be given. Diethoxymagnesium is particularly preferable.

Also, these dialkoxymagnesium may be obtained by reacting metallic magnesium with an alcohol in the presence of a halogen-containing organic metal compound or the like. The dialkoxymagnesium may be used alone or in combination or two or more.

The dialkoxymagnesium compound used is preferably in the form of granules or a powder and either amorphous or spherical in configuration. For example, when a spherical dialkoxymagnesium is used, a polymer powder having a better particle shape and a narrower particle size distribution can be obtained. This improves handling operability of the produced polymer powder during the polymerization operation and eliminates problems such as clogging of the filter or the like in the polymer separation device caused by fine particles contained in the produced polymer powder.

The spherical dialkoxy magnesium needs not necessarily be completely spherical, but may be oval or potato-shaped. Specifically, the particles may have a ratio (L/W) of the major axis diameter (L) to the minor axis diameter (W) usually of 3 or less, preferably of 1 to 2, and more preferably of 1 to 1.5.

Dialkoxy magnesium with an average particle size from 1 to 200 μm can be used. A more preferable average particle size is 5 to 150 μm. In the case of spherical dialkoxy magnesium, the average particle size is usually from 1 to 100 μm, preferably from 5 to 50 μm, and more preferably from 10 to 40 μm. A powder having a narrow particle size distribution with a small content of fine powder and coarse powder is preferably used. Specifically, the content of particles with a diameter of 5 μm or less should be 20% or less, and preferably 10% or less. On the other hand, the content of particles with a diameter of 100 μm or more should be 10% or less, and preferably 5% or less. Moreover, the particle size distribution shown by (D90/D10), wherein D90 is a particle size of 90% of the integrated particle size and D10 is a particle size of 10% of the integrated particle size, is 3 or less, and preferably 2 or less.

Methods for producing such spherical dialkoxymagnesium are described in, for example, JP-A-58-4132, JP-A-62-51633, JP-A-3-74341, JP-A-4-368391, and JP-A-8-73388.

The tetravalent titanium halide compound (b) (hereinafter referred to from time to time as "component (b)") used for the preparation of the component (A) in the present invention is one or more compounds selected from the group consisting of a titanium halide or alkoxytitanium halide shown by the formula $Ti(OR^7)_mX_{4-m}$, wherein $R^7$ represents an alkyl group having 1 to 4 carbon atoms, X represents a halogen atom, and n represents an integer satisfying the formula $0 \leqq m \geqq 4$.

Specific examples include, as titanium halides, titanium tetrahalides such as titanium tetrachloride, titanium tetrabromide, and titanium tetraiodide and, as alkoxytitanium halides, methoxytitanium trichloride, ethoxytitanium trichloride, propoxytitanium trichloride, n-butoxytitanium trichloride, dimethoxytitanium dichloride, diethoxytitanium dichloride, dipropoxytitanium dichloride, di-n-butoxytitanium dichloride, trimethoxytitanium chloride, triethoxytitanium chloride, tripropoxytitanium chloride, and tri-n-butoxy titanium chloride. Of these, titanium tetrahalides are preferable, with titanium tetrachloride being particularly preferable. These titanium compounds may be used either individually or in combination of two or more.

The electron donor compound (hereinafter referred to from time to time as "component (c)") used for preparing the solid catalyst component (A) is an organic compound containing an oxygen atom or a nitrogen atom. Alcohols, phenols, ethers, esters, ketones, acid halides, aldehydes, amines, amides, nitriles, isocyanates, and organosilicon compounds containing an Si—O—C bond or an Si—N—C bond can be given as examples.

As specific examples, alcohols such as methanol, ethanol, n-propanol, 2-ethylhexanol; phenols such as phenol and cresol; ethers such as dimethyl ether, diethyl ether, dipropyl ether, dibutyl ether, diamyl ether, diphenyl ether, 9,9-bis (methoxymethyl)fluorene, 2-isopropyl-2-iso-pentyl-1,3-dimethoxypropane, 2,2-diisobutyl-1,3-dimethoxypropane, 2,2-dicyclohexyl-1,3-dimethoxy propane, 2,2-bis(cyclohexylmethyl)-1,3-dimethoxypropane, 2-cyclohexyl-2-isopropyl-1,3-dimethoxypropane, 2-isopropyl-2-sec-butyl-1,3-dimethoxypropane, 2,2-diphenyl-1,3-dimethoxypropane, and 2-cyclopentyl-2-isopropyl-1,3-dimethoxypropane; monocarboxylic acid esters such as methyl formate, ethyl acetate, vinyl acetate, propyl acetate, octyl acetate, cyclohexyl acetate, ethyl propionate, ethyl butylate, ethyl benzoate, propyl benzoate, butyl benzoate, octyl benzoate, cyclohexyl benzoate, phenyl benzoate, methyl p-toluate, ethyl p-toluate, methyl anisate, and ethyl anisate; dicarboxylic acid esters such as diethyl malonate, dipropyl malonate, dibutyl malonate, diisobutyl malonate, dipentyl malonate, dineopentyl malonate, diethyl isopropylbromomalonate, diethyl butylbromomalonate, diethyl diisobutylbromomalonate, diethyl diisopropylmalonate, diethyl dibutylmalonate, diethyl diisobutylmalonate, diethyl diisopentylmalonate, diethyl isopropylbutylmalonate, dimethyl isopropylisopentylmalonate, diethyl bis(3-chloro-n-propyl)malonate, diethyl bis(3-bromo-n-propyl)malonate, diethyl maleate, dibutyl maleate, dimethyl adipate, diethyl adipate, dipropyl adipate, dibutyl adipate, diisodecyl adipate, dioctyl adipate, phthalic acid diesters, and phthalic acid diester derivatives; ketones such as acetone, methyl ethyl ketone, methyl butyl ketone, acetophenone, and benzophenone; acid chlorides such as phthalic acid dichloride and terephthalic acid dichloride; aldehydes such as acetaldehyde, propylaldehyde, octylaldehyde, and benzaldehyde; amines such as methylamine, ethylamine, tributylamine, piperidine, aniline, and pyridine; amides such as olefin acid amide and stearic acid amide; nitriles such as acetonitrile, benzonitrile, and tolylnitrile; isocyanates such as methyl isocyanate and ethyl isocyanate; organosilicon compounds containing an Si—O—C bond such as phenylalkoxysilane, alkylalkoxysilane, phenylalkylalkoxysilane, cycloalkylalkoxysilane, and cycloalkylalkylalkoxysilane, and organosilicon compounds having an Si—N—C bond such as an aminoalkoxysilane shown by the above-mentioned formula (1), bis(alkylamino)dialkoxysilane, bis(cycloalkylamino)dialkoxysilane, alkyl(alkylamino)dialkoxysilane, dialkylaminotrialkoxysilane, and cycloalkylaminotrialkoxysilane can be given. As specific examples of the aminoalkoxysilane compound of the above formula (1), the same compounds mentioned above can be given.

Among the above electron donor compounds, the esters, particularly aromatic dicarboxylic acid diesters, are preferably used. Phthalic acid diester and phthalic acid diester derivatives are ideal compounds. Specific examples of the phthalic acid diester include the following compounds: dimethyl phthalate, diethyl phthalate, di-n-propyl phthalate, diisopropyl phthalate, di-n-butyl phthalate, diisobutyl phthalate, ethyl(methyl)phthalate, methyl(isopropyl) phthalate, ethyl(n-propyl) phthalate, ethyl(n-butyl) phthalate, ethyl (isobutyl) phthalate, di-n-pentyl phthalate, diisopentyl phthalate, dineopentyl phthalate, dihexyl phthalate, di-n-heptyl phthalate, di-n-octyl phthalate, bis(2,2-dimethylhexyl) phthalate, bis(2-ethylhexyl) phthalate, di-n-nonyl phthalate, diisodecyl phthalate, bis(2,2-dimethylheptyl) phthalate, n-butyl(isohexyl) phthalate, n-butyl(2-ethylhexyl) phthalate, n-pentyl(hexyl) phthalate, n-pentyl(isohexyl) phthalate, isopentyl(heptyl) phthalate, n-pentyl(2-ethylhexyl) phthalate, n-pentyl(isononyl) phthalate, isopentyl(n-decyl) phthalate, n-pentyl(undecyl) phthalate, isopentyl(isohexyl) phthalate, n-hexyl(2,2-dimethylhexyl) phthalate, n-hexyl(isononyl) phthalate, n-hexyl(n-decyl) phthalate, n-heptyl(2-ethylhexyl) phthalate, n-heptyl(isononyl) phthalate, n-heptyl(neodecyl) phthalate, and 2-ethylhexyl(isononyl) phthalate. One or more of these compounds can be used.

As examples of the phthalic acid diester derivatives, compounds in which one or two hydrogen atoms on the benzene ring to which the two ester groups of the phthalic diesters bond are replaced with an alkyl group having 1 to 5 carbon atoms or a halogen atom such as a chlorine atom, a bromine atom, and a fluorine atom can be given. The solid catalyst component prepared by using the phthalic acid diester derivatives as an electron donor compound can particularly contribute to a melt flow rate increase with a given amount of hydrogen by increasing hydrogen response, that is, can increase the melt flow rate of polymer by using the same or a smaller amount of hydrogen during polymerization. As specific examples, dineopentyl 4-methylphthalate, dineopentyl 4-ethylphthalate, dineopentyl 4,5-dimethylphthalate, dineopentyl 4,5-diethylphthalate, diethyl 4-chlorophthalate, di-n-butyl 4-chlorophthalate, dineopentyl 4-chlorophthalate, diisobutyl 4-chlorophthalate, diisohexyl 4-chlorophthalate, diisooctyl 4-chlorophthalate, diethyl 4-bromophthalate, di-n-butyl 4-bromophthalate, dineopentyl 4-bromophthalate, diisobutyl 4-bromophthalate, diisohexyl 4-bromophthalate, diisooctyl 4-bromophthalate, diethyl 4,5-dichlorophthalate, di-n-butyl 4,5-dichlorophthalate, diisohexyl 4,5-dichlorophthalate, and diisooctyl 4,5-dichlorophthalate can be given. Among these, dineopentyl 4-bromophthalate, di-n-butyl 4-bromophthalate, and diisobutyl 4-bromophthalate are preferable.

The above ester compounds are also preferably used in combination of two or more. In this instance, the esters are preferably combined so that the total carbon atoms in the alkyl group possessed by one ester may differ by four or more from that possessed by another ester.

The component (A) of the present invention can be preferably prepared by causing the above components (a), (b), and (c) to come in contact with each other in the presence of an aromatic hydrocarbon compound (d) (hereinafter may be simply referred to as "component (d)"). Aromatic hydrocarbon compounds having a boiling point of 50° C. to 150° C. such as toluene, xylene, and ethylbenzene are preferably used as the component (d). These aromatic hydrocarbons can be used either individually or in combination of two or more.

As a preferable method for preparing the component (A) of the present invention, a method of preparing a suspension liquid of the component (a), the component (c), and the aromatic hydrocarbon compound (d) having a boiling point of 50 to 150° C., causing this suspension liquid to contact a mixed solution made from the component (b) and the component (d), and reacting the mixture can be given.

In the preparation of the solid catalyst component (A) of the present invention, in addition to the above components, a polysiloxane (hereinafter may be simply referred to as "component (e)") can be preferably used to improve the stereoregularity or crystallinity of the formed polymer and to reduce the amount of fine polymer particles. Polysiloxanes are polymers having a siloxane bond (—Si—O bond) in the main chain and are generally referred to as silicone oil. The polysiloxanes used in the present invention are chain-structured, partially hydrogenated, cyclic or modified polysiloxanes which are liquid or viscous at normal temperature with a viscosity at 25° C. in the range of 0.02 to 100 s/cm$^2$ (2 to 10,000 cSt).

As examples of the chain-structured polysiloxanes, dimethylpolysiloxane and methylphenylpolysiloxane can be given; as examples of the partially hydrogenated polysiloxanes, methyl hydrogen polysiloxanes with a hydrogenation degree of 10 to 80% can be given; as examples of the cyclic polysiloxanes, hexamethylcyclotrisiloxane, octamethylcyclotetrasiloxane, decamethylcyclopentasiloxane, 2,4,6-trimethylcyclotrisiloxane, and 2,4,6,8-tetramethylcyclotetrasiloxane can be given; as examples of the modified polysiloxane, higher fatty acid group-substituted dimethylsiloxane, epoxy group-substituted dimethylsiloxane, and polyoxyalkylene group-substituted dimethylsiloxane can be given. Of these, decamethylcyclopentasiloxane and dimethylpolysiloxane are preferable, with decamethylcyclopentasiloxane being particularly preferable.

The component (A) in the present invention is prepared by causing the above components (a), (b), and (c), and, as required, the component (d) or component (e) to come in contact with each other. The method of preparing the component (A) is described below in detail. One specific example of the method for preparing the component (A) comprises suspending the magnesium compound (a) in an alcohol, a halogenated hydrocarbon solvent, the tetravalent titanium halide (b), or the aromatic hydrocarbon compound (d), and causing the electron donor compound (c) such as a phthalic acid diester and/or the tetravalent titanium halide (b) to come in contact with the suspension. In this method, the component (A) in the form of spherical particles with a sharp particle size distribution can be obtained by using a spherical magnesium compound. Such a component (A) in the form of spherical particles with a sharp particle size distribution can also be obtained without using a spherical magnesium compound 1f particles are formed by a spray dry method in which a solution or a suspension liquid is sprayed and dried using a sprayer, for example.

These components are caused to come in contact with each other in a vessel equipped with a stirrer in an inert gas atmosphere from which water and the like have been removed while stirring. The contact temperature, which is a temperature at which these components are caused to come into contact with each other, may be either the same as or different from the reaction temperature. When the components are caused to come into contact with each other by stirring for preparing the mixture or are dispersed or suspended for a denaturing treatment, the components may be stirred at a comparatively low temperature of around room temperature. A temperature in a range from 40 to 130° C. is preferable for obtaining the product by reaction after contact. The reaction does not proceed sufficiently at a reaction temperature below 40° C., resulting in a solid catalyst component with inadequate properties. On the other hand, control of the reaction becomes difficult at a temperature above 130° C. due to vaporization of the solvent and the like. The reaction time is one minute or more, preferably ten minutes or more, and still more preferably 30 minutes or more.

As preferable processes for preparing the component (A) of the present invention, a process comprising suspending the component (a) in the component (d), causing the resulting suspension to come in contact with the component (b), then the component (c) and component (d), and causing these components to react; and a process comprising suspending the component (a) in the component (d), causing the resulting suspension liquid to come in contact with the component (c), then the component (b), and causing these components to react can be given. The component (A) thus prepared may be caused to come in contact with the component (b) or the components (b) and (c) once or two or more times to improve the performance of the ultimate solid catalyst component. This contacting step is preferably carried out in the presence of the aromatic hydrocarbon (d).

As a preferable method for preparing the component (A) of the present invention, a method of preparing a suspension liquid of the component (a), the component (c), and the aromatic hydrocarbon compound (d) having a boiling point of 50 to 150° C., causing this suspension liquid to contact with a mixed solution of the component (b) and the component (d), and reacting the mixture can be given.

As a preferable example of the method for preparing the component (A), the following method can be given. A suspension is prepared from the above component (a), component (c), and an aromatic hydrocarbon compound (d) having a boiling point of 50 to 150° C. A mixed solution is prepared from the above component (c) and the aromatic hydrocarbon compound (d) having a boiling point of 50 to 150° C. The above-described suspension liquid is added to this solution. The resulting mixture is heated and reacted (a primary reaction). After the reaction, the solid product is washed with a hydrocarbon compound which is liquid at normal temperature to obtain a solid product. Furthermore, an additional component (b) and the aromatic hydrocarbon compound (d) having a boiling point of 50 to 150° C. may be caused to come in contact with the washed solid product at a temperature of −20 to 100° C. The temperature is raised to react the mixture (a secondary reaction), and after the reaction, the reaction mixture is washed with a hydrocarbon compound, which is liquid at normal temperature, one to ten times to obtain the component (A).

Based on the above description, a particularly preferable process for preparing the solid catalyst component (A) comprises suspending the dialkoxymagnesium compound (a) in the aromatic hydrocarbon compound (d) having a boiling point in the range of 50-150° C., causing the tetravalent titanium halide (b) to contact the suspension, and reacting the mixture. In this instance, one or more electron donor compounds (c) such as phthalic acid diester are caused to come in contact with the suspension liquid at a temperature from −20 to 130° C., either before or after the tetravalent titanium halide compound (b) is contacted, then optionally, the component (e) is contacted and reacted to obtain a solid product (1). In this instance, it is desirable to carry out an aging reaction at low temperature either before or after the above one or more electron donor compounds are caused to come in contact with the suspension liquid. After washing the solid product (1) with a hydrocarbon compound which is liquid at normal temperature (intermediate washing), the tetravalent titanium halide (b) is again caused to contact and react with the solid product (1) in the presence of the aromatic hydrocarbon compound at a temperature of −20 to 100° C. to obtain a solid reaction product (2). As required, the intermediate washing and the reaction may be further repeated several times. Subsequently, the solid product (2) is washed with a liquid hydrocarbon compound by decantation at normal temperature to obtain the solid catalyst component (A).

The ratio of the components used for the preparation of the solid catalyst component (A) cannot be generically defined, because such a ratio varies according to the method of preparation employed. For example, the tetravalent titanium halide (b) is used in an amount from 0.5 to 100 mol, preferably from 0.5 to 50 mol, still more preferably from 1 to 10 mol; the electron donor compound (c) is used in an amount from 0.01 to 10 mol, preferably from 0.01 to 1 mol, and still more preferably from 0.02 to 0.6 mol; the aromatic hydrocarbon compound (d) is used in an amount from 0.001 to 500 mol, preferably from 0.001 to 100 mol, and still more preferably from 0.005 to 10 mol; and the polysiloxane (e) is used in an amount from 0.01 to 100 g, preferably from 0.05 to 80 g, and still more preferably from 1 to 50 g, for one mol of the magnesium compound (a).

Although there are no specific limitations to the amounts of titanium, magnesium, halogen atoms, and electron donors in the solid catalyst component (A), the content of titanium is from 0.5 to 8.0 wt %, preferably from 1.0 to 8.0 wt %, and still more preferably from 2.0 to 8.0 wt %; the content of magnesium is from 10 to 70 wt %, preferably from 10 to 50 wt %, more preferably from 15 to 40 wt %, and particularly preferably from 15 to 25 wt %; the content of halogen atoms is from 20 to 90 wt %, preferably from 30 to 85 wt %, more preferably from 40 to 80 wt %, and particularly preferably from 45 to 75 wt %; and the total amount of electron donor compounds is from 0.5 to 30 wt %, preferably from 1 to 25 wt %, and particularly preferably from 2 to 20 wt %.

Any compounds shown by the above formula (2) can be used without any specific limitations as the organoaluminum compound (B) (hereinafter referred to from time to time simply as "component (B)") for preparing the catalyst for the polymerization of olefins of the present invention. In the above formula (2), $R^6$ is preferably an ethyl group or an isobutyl group; Q is preferably a hydrogen atom, a chlorine atom, or a bromine atom; and p is preferably 2 or 3, and particularly preferably 3. As specific examples of such an organoaluminum compound (B), triethylaluminum, diethylaluminum chloride, triisobutylaluminum, diethylaluminum bromide, and diethylaluminum hydride can be given. These compounds may be used either individually or in combination of two or more. Triethylaluminum and triisobutylaluminum are preferably used.

The compounds shown by the above formula (1) can be given as the aminosilane compound (C) (hereinafter may be referred to from time to time as "component (C)") which can be used for preparing the catalyst for olefin polymerization of the present invention. Specific examples include the above-mentioned compounds.

In addition to the above components, an organosilicon compound other than the above-described aminosilane compound (hereinafter may be simply referred to as "component (D)") may be used for preparing the catalyst for olefin polymerization of the present invention. As examples of the organosilicon compound (D), a tetraalkoxysilane, an alkylalkoxysilane, an alkyl(cycloalkyl)alkoxysilane, a cycloalkylalkoxysilane, a phenylalkoxysilane, an alkyl(phenyl)alkoxysilane, an alkyl(alkylamino)alkoxysilane, an alkylaminoalkoxysilane, a cycloalkyl(alkylamino)alkoxysilane, an alkyl(cycloalkylamino)alkoxysilane, a polycyclic aminoalkoxysilane, and an alkyl(polycyclic amino)alkoxysilane can be given.

Specific examples of the organosilicon compound (D) include tetramethoxysilane, tetraethoxysilane, triethoxychlorosilane, diethoxydichlorosilane, di-n-propyldimethoxysilane, diisopropyldimethoxysilane, di-n-butyldimethoxysilane, di-n-butyldiethoxysilane, t-butyl(methyl)dimethoxysilane, t-butyl(ethyl)dimethoxysilane, dicyclohexyldimethoxysilane, cyclohexyl(methyl)dimethoxysilane, dicyclopentyldimethoxysilane, cyclopentyl(methyl)diethoxysilane, cyclopentyl(ethyl)dimethoxysilane, cyclopentyl(cyclohexyl)dimethoxysilane, 3-methylcyclohexyl(cyclopentyl)dimethoxysilane, 4-methylcyclohexyl(cyclopentyl)dimethoxysilane, 3,5-dimethylcyclohexyl(cyclopentyl)dimethoxysilane, bis(diethylamino)dimethoxysilane, bis(di-n-propylamino)dimethoxysilane, bis(di-n-butylamino)dimethoxysilane, bis(di-t-butylamino)dimethoxysilane, bis(dicyclopentylamino)dimethoxysilane, bis(dicyclohexylamino)dimethoxysilane, bis(di-2-methylcyclohexylamino)dimethoxysilane, bis(perhydroisoquinolino)dimethoxysilane, bis(perhydroquinolino)dimethoxysilane, bis(ethyl-n-propylamino)dimethoxysilane, bis(ethylisopropylamino)dimethoxysilane, bis(ethyl-n-butylamino)dimethoxysilane, bis(ethylisobutylamino)dimethoxysilane, bis(ethyl-t-butylamino)dimethoxysilane, bis(isobutyl-n-propylamino)dimethoxysilane, bis(ethylcyclopentylamino)dimethoxysilane, bis(ethylcyclohexylamino)dimethoxysilane, ethyl(diethylamino)dimethoxysilane, n-propyl(diisopropylamino)dimethoxysilane, isopropyl(di-t-butylamino)dimethoxysilane, cyclohexyl(diethylamino)dimethoxysilane, ethyl(di-t-butylamino)dimethoxysilane, ethyl(perhydroisoquinolino)dimethoxysilane, n-propyl(perhydroisoquinolino)dimethoxysilane, isopropyl(perhydroisoquinolino)dimethoxysilane, n-butyl(perhydroisoquinolino)dimethoxysilane, ethyl(perhydroquinolino)dimethoxysilane, n-propyl(perhydroquinolino)dimethoxysilane, isopropyl(perhydroquinolino)dimethoxysilane, n-butyl(perhydroquinolino)dimethoxysilane, bis(diethylamino)diethoxysilane, bis(di-n-propylamino)diethoxysilane, bis(di-n-butylamino)diethoxysilane, bis(di-t-butylamino)diethoxysilane, bis(dicyclopentylamino)diethoxysilane, bis(dicyclohexylamino)diethoxysilane, bis(di-2-methylcyclohexylamino)diethoxysilane, bis(diperhydroisoquinolino)diethoxysilane, bis(diperhydroquinolino)diethoxysilane, bis(ethyl-n-propylamino)diethoxysilane, bis(ethylisopropylamino)diethoxysilane, bis(ethyl-n-butylamino)diethoxysilane, bis(ethyl-isobutylamino)diethoxysilane, bis(ethyl-t-butylamino)diethoxysilane, bis(isobutyl-n-propylamino)diethoxysilane, bis(ethylcyclopentylamino)diethoxysilane, bis(ethylcyclohexylamino)diethoxysilane, n-propyl(diisopropylamino)diethoxysilane, ethyl(perhydroisoquinolino)diethoxysilane, n-propyl(perhydroisoquinolino)diethoxysilane, isopropyl(perhydroisoquinolino)diethoxysilane, n-butyl(perhydroisoquinolino)diethoxysilane, ethyl(perhydroquinolino)diethoxysilane, n-propyl(perhydroquinolino)diethoxysilane, isopropyl(perhydroquinolino)diethoxysilane, n-butyl(perhydroquinolino)diethoxysilane, thexyltrimethoxysilane, diethylaminotrimethoxysilane, di-n-propylaminotrimethoxysilane, di-n-butylaminotrimethoxysilane, di-t-butylaminotrimethoxysilane, dicyclopentylaminotrimethoxysilane, dicyclohexylaminotrimethoxysilane, di-2-methylcyclohexylaminotrimethoxysilane, perhydroisoquinolinotrimethoxysilane, perhydroquinolinotrimethoxysilane, diethylaminotriethoxysilane, di-n-propylaminotriethoxysilane, di-n-butylaminotriethoxysilane, ethyl-t-butylaminotriethoxysilane, ethyl-sec-butylaminotriethoxysilane, dicyclopentylaminotriethoxysilane, dicyclohexylaminotriethoxysilane, di-2-methylcyclohexylaminotriethoxysilane, perhydroisoquinolinotriethoxysilane, perhydroquinolinotriethoxysilane, bis(t-butylamino)dimethoxysilane, bis(cyclohexylamino)dimethoxysilane, bis(t-butylamino)diethoxysilane, bis(cyclohexylamino)diethoxysilane, trivinylmethylsilane, and tetravinyl silane. These compounds may be used either individually or in combination of two or more as the organosilicon compound (D).

According to the process for manufacturing olefin polymers of the present invention, olefins are polymerized or copolymerized by random or block copolymerization in the presence of the catalyst for olefin polymerization of the present invention. The olefins such as ethylene, propylene, 1-butene, 1-pentene, 4-methyl-1-pentene, and vinyl cyclohexane can be used either individually or in combination of two or more. Of these, ethylene, propylene, and 1-butene can be suitably used. A particularly preferable olefin is propylene. Propylene may be copolymerized with other olefins. As the olefins to be copolymerized, ethylene, 1-butene, 1-pentene, 4-methyl-1-pentene, vinyl cyclohexane, and the like can be used either individually or in combination of two or more. Of these, ethylene and 1-butene can be suitably used. As the method for copolymerizing propylene with other olefins, random copolymerization of polymerizing propylene with a small amount of ethylene as a comonomer in one step, and propylene-ethylene block copolymerization of polymerizing only propylene in a first step (first polymerization vessel) and copolymerizing propylene and ethylene in a second step (second polymerization vessel) or more steps (multiple stage polymerization vessel) are typical methods. The catalyst of the present invention comprising the component (A), component (B), and component (C) is effective in both the random copolymerization and block copolymerization for improving the catalytic activity, stereoregularity, and/or hydrogen response, copolymerization performance, and properties of resulting copolymers.

In addition to the catalyst component (C), the above-described component (D) may be used. The components (C) and (D) may be used either as a mixture or separately in a multiple stage polymerization vessel of the block copolymerization. A known electron donor compound such as an alcohol, oxygen gas, or a ketone may be added to the polymerization reaction system in order to prevent formation of gel in a finished product, particularly when shifting from homopolymerization of propylene to the block copolymerization. As specific examples of the alcohol, ethyl alcohol and isopropyl alcohol can be given. These alcohols are used in an amount of 0.01 to 10 mol, and preferably 0.1 to 2 mol, for one mol of the component (B).

The ratio of each component used is not specifically limited inasmuch as such a ratio does not influence the effect of the present invention. Usually, the component (B) is used in an amount of 1 to 2,000 mol, and preferably 50 to 1,000 mol per one mol of titanium atom in the component (A). The component (C) is used in an amount of 0.002 to 10 mol, preferably 0.01 to 2 mol, and particularly preferably 0.1 to 0.5 mol per one mol of the component (B). If the component (D) is used in combination, the amount is 0.002 to 10 mol, preferably 0.01 to 2 mol, and particularly preferably 0.01 to 0.5 mol per one mol of the component (B), and in the amount of 0.001 to 10 mol, preferably 0.01 to 10 mol, and particularly preferably 0.01 to 2 mol per one mol of the component (C).

Although the order of contact of these components is optional, it is desirable to first add the organoaluminum compound (B) to the polymerization system, then cause the amino silane compound (C) or a mixture of the components (C) and (D) to contact the organoaluminum compound (B), or cause the component (C) and component (D) in an optional order to contact the organoaluminum compound (B) and cause the solid catalyst component (A) to contact the resulting mixture. A method of forming a catalyst by adding the organoaluminum compound (B) to the polymerization system, separately causing the component (A) to contact the component (C) or the components (C) and (D), and feeding the contacted component (A) and component (C) or the components (C) and (D) to the polymerization system is also a preferable embodiment. It is possible to further improve the hydrogen response of the catalyst and crystalline properties of the resulting polymer by using a previously contacted mixture of the component (A) with the component (B) or the component (C), and the component (D).

In the present invention, polymerization can be carried out either in the presence or in the absence of an organic solvent. Olefin monomers such as propylene may be used either in a gaseous state or in a liquid state. The polymerization reaction is preferably carried out at a temperature of 200° C. or less, and preferably at 150° C. or less, under a pressure of 10 MPa or less, and preferably 6 MPa or less. Either a continuous polymerization system or a batch polymerization system may be used for the polymerization reaction. In addition, the polymerization can be completed either in one step or in two or more steps.

In polymerizing olefins using the catalyst formed from the component (A), component (B), and component (C) (hereinafter may be referred to from time to time as "main polymerization"), it is desirable to preliminarily polymerize the olefins prior to the main polymerization to further improve the catalyst activity, stereoregularity, properties of resulting polymer particles, and the like. In addition to the olefins used in the main polymerization, monomers such as styrene can be used in the preliminary polymerization. Specifically, after causing the component (A) to contact the component (B) and/or the component (C) in the presence of olefins to preliminarily polymerize 0.1 to 100 g of the polyolefins for 1 g of the component (A), the component (B) and/or the component (C) are further caused to contact to form the catalyst. In the case where the component (D) is used in combination, it is possible to cause the component (A) to contact the components (B) and (D) in the presence of olefins during the preliminary polymerization and to use the component (C) during the main polymerization.

Although the order of contact of the components and monomers in the preliminary polymerization is arbitrary, it is desirable to first add the component (B) to the preliminary polymerization system in an inert gas or in an atmosphere of a gas to be polymerized such as propylene, cause to come in contact with the component (C) and/or the component (D), and then with the component (A), and then cause an olefin such as propylene and/or one or more other olefins to come in contact with the mixture. Although not specifically limited, the preliminary polymerization temperature is from −10° C. to 70° C., and preferably from 0° C. to 50° C.

The polymerization of olefins in the presence of the olefin polymerization catalyst of the present invention can produce olefin polymers having higher stereoregularity of the polymer and improved hydrogen response than in the polymerization using a known catalyst. In addition, depending on the structure of the component (C), the catalytic activity and stereoregularity are improved as compared with the case in which a commonly-used catalyst is used. Specifically, when the catalyst of the present invention is used for polymerization of olefins, it has been confirmed that the hydrogen response is improved while maintaining high stereoregularity depending on the structure of the component (C). In addition, it has been confirmed that the effect of improving the catalytic activity and stereoregularity can be promoted by using of the component (C) having an appropriate structure.

The present invention will be described in more detail by examples, which should not be construed as limiting the present invention.

Example 1

Synthesis of Aminosilane Compound 1

A three-necked flask of which the internal atmosphere was sufficiently purged with nitrogen gas was charged with 70 ml of a THF solution containing 0.1 mol of methylamine in a nitrogen stream. The solution was cooled to −10° C. while stirring. 50 ml of a hexane solution containing 0.1 mol of BuLi was slowly added dropwise to the amine solution using a dripping funnel. After the addition, the mixture was gradually heated and reacted at 50° C. for three hours, thereby obtaining a slurry of Mg salt of methylamine. A three-necked flask of which the internal atmosphere was sufficiently purged with nitrogen gas was charged with 80 ml of a toluene solution containing 0.1 mol of bis(perhydroisoquinolino) dimethoxysilane synthesized by a common method in a nitrogen stream. The solution was cooled to −10° C. The abovementioned slurry of Li salt of methylamine was slowly added to the toluene solution using an injector. After the addition, the mixture was gradually heated and reacted at 60° C. for five hours. After the reaction, the solid was separated from the liquid by centrifugation in a nitrogen stream and washed twice with 20 ml of toluene. The washing solution was added to the liquid portion. The solvent was evaporated under reduced pressure from the liquid portion and the main product of bis(perhydroisoquinolino)(methylamino)methoxysilane was purified by distillation under reduced pressure. As a result of elementary analysis, the compound was found to consists of C, 65.30% (65.70%), H, 10.52% (10.75%), N, 11.39% (11.49%), wherein the percentages in the parentheses are theoretical values.

Example 2

Synthesis of Aminosilane Compound 2

A three-necked flask of which the internal atmosphere was sufficiently purged with nitrogen gas was charged with 70 ml of a toluene solution containing 0.1 mol of di-t-butylamine in a nitrogen stream. The solution was cooled to −10° C. while stirring. 50 ml of a diisopropyl ether solution containing 0.1 mol of BuMgCl was slowly added dropwise to the amine solution using a dripping funnel. After the addition, the mixture was gradually heated and reacted at 50° C. for three hours, thereby obtaining a slurry of Mg salt of di-t-butylamine. A slurry of Mg salt of di-t-butylamine and methylamine was obtained in the same synthesis method. A three-necked flask of which the internal atmosphere was sufficiently purged with nitrogen gas was charged with 70 ml of a toluene solution containing 0.05 mol of tetramethoxysilane in a nitrogen stream. The solution was cooled to −10° C. while stirring. A slurry of Mg salt containing 0.05 mol of di-t-butylamine was added to the toluene solution in a nitrogen stream using a dripping funnel. The mixture was reacted at 60° C. for three hours and then cooled to −10° C. A slurry of Mg salt containing equimolar di-t-butylamine was slowly added dropwise in a nitrogen stream. After the addition, the mixture was heated to 60° C. and reacted for three hours. The mixture was cooled to −10° C. A slurry of Mg salt containing equimolar methylamine was added, heated to 60° C., and reacted for five hours in the same manner. After the reaction, the produced solid was separated from the liquid in a nitrogen stream by a centrifugal method. The solid was washed twice with 20 ml of toluene. The washing solution was added to the liquid portion. The solvent was evaporated under reduced pressure from the liquid portion and the main product of (di-t-butylamino)(t-butylamino)(methylamino)methoxysilane was purified by distillation under reduced pressure. As a result of elementary analysis, the compound was found to consist of C, 59.30% (59.35%), H, 12.32% (12.29%), N, 13.49% (13.84%), wherein the percentages in the parentheses are theoretical values.

Example 3

Synthesis of Aminosilane Compound 3

A three-necked flask of which the internal atmosphere was sufficiently purged with nitrogen gas was charged with 60 ml of a toluene solution containing 0.1 mol of perhydroisoquinoline. The solution was cooled to −10° C. while stirring. 60 ml of a hexane solution containing 0.1 mol of butyllithium, which was prepared by diluting commercially available hexane solution of butyllithium with hexane, was slowly added dropwise to the toluene solution at −10° C. in a nitrogen stream using a dripping funnel. After the addition, the mixture was gradually heated and reacted at 60° C. for two hours, thereby obtaining a slurry of lithium salt of perhydroisoquinoline. Mg salt containing 0.1 mol of methylamine was prepared in the same manner as in Example 1. A three-necked flask of which the internal atmosphere was sufficiently purged with nitrogen gas was charged with 60 ml of a toluene solution containing 0.05 mol of ethyltrimethoxysilane. The solution was cooled to −10° C. while stirring. A slurry of lithium salt containing 0.05 mol of perhydroisoquinoline was slowly added dropwise to the cooled solution using a dripping funnel. After the addition, the mixture was heated to 60° C. and reacted for four hours. After the reaction, the mixture was again cooled to −10° C. A slurry of Mg salt containing 0.05 mol of methylamine was slowly added dropwise to the cooled mixture in a nitrogen stream. After the addition, the mixture was heated to 70° C. and reacted for five hours. After the reaction, the produced solid was separated in a nitrogen stream by a centrifugal method. The solid was washed twice with 20 ml of toluene. The washing solution was added to the liquid portion. The solvent was evaporated under reduced pressure from the liquid portion and the main product of (perhydroisoquinolino)(methylamino)ethylmethoxysilane was purified by distillation under reduced pressure. As a result of elementary analysis, the compound was found to consist of C, 59.65% (60.88%), H, 11.12% (11.00%), N: 10.59% (10.92%), wherein the percentages in the parentheses are theoretical values.

Example 4

Synthesis of Aminosilane Compound 4

A slurry of lithium salt containing 0.1 mol of perhydroisoquinoline was synthesized in the same manner as in Example 3. A three-necked flask of which the internal atmosphere was sufficiently purged with nitrogen gas was charged with 50 ml of a toluene solution containing 0.06 mol of tetramethoxysilane. The solution was cooled to −10° C. while stirring. 30 ml of a slurry containing 0.06 mol of the above synthesized lithium salt of perhydroisoquinoline was slowly added dropwise in a nitrogen stream using a dripping funnel. After the addition, the mixture was gradually heated and reacted at 70° C. for five hours. The mixture was cooled to −10° C. while stirring. A three-necked flask of which the internal atmosphere was sufficiently purged with nitrogen gas was charged with 40 ml of a THF solution containing 0.06 mol of methylamine. The solution was cooled to −10° C. while stirring. 40 ml of a hexane solution containing 0.06 mol of butyllithium, which was prepared by diluting commercially available hexane solution of butyllithium with hexane, was slowly added dropwise to the THF solution. After the addition, the mixture was reacted at 40° C. for two hours, thereby obtaining a slurry of lithium salt of methylamine. All the slurry of lithium salt of methylamine was slowly added to the cooled mixture in a nitrogen stream while stirring. After the addition, the mixture was heated to 70° C. and reacted for five hours. After the reaction, the produced solid was separated in a nitrogen stream by a centrifugal method. The solid was washed twice with 20 ml of toluene. The washing solution was added to the separated liquid portion. The solvent was evaporated under reduced pressure from the liquid portion and the main product of bis(perhydroisoquinolino)(ethylamino)methoxysilane was purified by distillation under reduced pressure. As a result of elementary analysis, the compound was found to consist of C, 66.55% (66.44%), H, 10.45% (10.39%), N, 10.90% (11.07%), wherein the percentages in the parentheses are theoretical values.

Example 5

Synthesis of Aminosilane Compound 5

A three-necked flask of which the internal atmosphere was sufficiently purged with nitrogen gas was charged with 50 ml of a toluene solution containing 0.1 mol of diethylamine. The solution was cooled to −10° C. while stirring. 50 ml of a diisopropyl ether solution containing 0.1 mol of BuMgCl was slowly added dropwise to the ethylamine solution using a dripping funnel. After the addition, the mixture was gradually heated and reacted at 50° C. for three hours, thereby obtaining a slurry of Mg salt of ethylamine. A slurry of Mg salt containing 0.1 mol of diethylamine was obtained in the same manner. A three-necked flask of which the internal atmosphere was sufficiently purged with nitrogen gas was charged with 60 ml of a toluene solution containing 0.05 mol of tetraethoxysilane. The solution was cooled to −10° C. while stirring. All the slurry of Mg salt of ethylamine prepared above was slowly added to the solution using a dripping funnel. After the addition, the mixture was heated to 60° C. and reacted for three hours. After the reaction, the mixture was cooled to −10° C. while stirring. A slurry of Mg salt containing 0.05 mol of diethylamine was added dropwise to the mixture in the same manner. After the addition, the mixture was gradually heated and reacted at 70° C. for four hours. After the reaction, the produced solid was separated from the liquid in a nitrogen stream by a centrifugal method. The solid was washed twice with 20 ml of toluene. The washing solution was added to the liquid. The solvent was evaporated under reduced pressure from the solution and the main product of bis(ethylamino)(diethylamino)ethoxysilane was purified by distillation under reduced pressure. As a result of elementary analysis, the compound was found to consist of C, 51.55% (51.45%), H, 11.45% (11.66%), N, 17.90% (18.00%), wherein the percentages in the parentheses are theoretical values.

Example 6

Synthesis of Aminosilane Compound 6

120 ml of a slurry of Mg salt containing 0.1 mol of di-t-butylamine was obtained in the same manner as in Example 2. 70 ml of a slurry of Mg salt containing 0.05 mol of ethylamine was obtained in the same manner as in Example 5. A three-necked flask of which the internal atmosphere was sufficiently purged with nitrogen gas was charged with 60 ml of a toluene solution containing 0.05 mol of tetraethoxysilane. The solution was cooled to −10° C. while stirring. 60 ml of a slurry of Mg salt containing 0.05 mol of di-t-butylamine was slowly added dropwise to the cooled solution in a nitrogen stream. After the addition, the mixture was gradually heated and reacted at 60° C. for three hours. After the reaction, the slurry of the mixture was cooled to −10° C. 70 ml of a slurry of Mg salt containing 0.05 mol of ethylamine was slowly added dropwise to the slurry of the mixture in a nitrogen stream. After the addition, the mixture was gradually heated and reacted at 70° C. for five hours. After the reaction, the produced solid was separated from the liquid in a nitrogen stream by a centrifugal method. The solid was washed twice with 20 ml of toluene. The washing solution was added to the liquid. The solvent was evaporated under reduced pressure from the solution and the main product of (di-t-butylamino)(ethylamino)diethoxysilane was purified by distillation under reduced pressure. As a result of elementary analysis, the compound was found to consist of C, 57.75% (57.88%), H, 11.65% (11.80%), N, 9.55% (9.64%), wherein the percentages in the parentheses are theoretical values.

Example 7

Preparation of Solid Catalyst Component 1

A 2,000 ml round bottom flask equipped with a stirrer, of which the internal atmosphere had been sufficiently replaced with nitrogen gas, was charged with 150 g of diethoxymagnesium and 750 ml of toluene to prepare a suspension. The suspension liquid was added to a solution of 450 ml of toluene and 300 ml of titanium tetrachloride previously filled in another 2,000 ml round bottom flask equipped with a stirrer, of which the internal atmosphere had been sufficiently replaced with nitrogen gas. The suspension liquid was reacted at 5° C. for one hour. After the addition of 22.5 ml of n-butyl phthalate, the mixture was heated to 100° C. and reacted for two hours while stirring. After the reaction, the resulting reaction mixture was washed four times with 1,300 ml of toluene at 80° C. 1,200 ml of toluene and 300 ml of titanium tetrachloride were added to the washed product and the mixture was heated to 110° C. and reacted for two hours while stirring. The intermediate washing and the secondary treatment were repeated once more. The resulting reaction mixture was washed seven times with 1,300 ml of heptane at 40° C., filtered, and dried to obtain a solid catalyst component in the form of a powder. The content of titanium in the solid component was measured and found to be 3.1 wt %.

Preparation of Polymerization Catalyst and Polymerization

A 2.0 l autoclave equipped with a stirrer, of which the internal atmosphere had been entirely replaced with nitrogen gas, was charged with 1.32 mmol of triethylaluminum, 0.13 mmol of bis(perhydroisoquinolino)(methylamino)methoxysilane obtained in Example 1, and the above solid catalyst component in an amount, in terms of the titanium atom contained therein, of 0.0026 mmol, thereby forming a polymerization catalyst. Then, with the addition of 4 l of hydrogen gas and 1.4 l of liquified propylene, preliminary polymerization was carried out for five minutes at 20° C., following which the preliminary polymerization product was heated and polymerization was carried out for one hour at 70° C. The catalyst activity, bulk density (BD, g/ml), heptane insoluble components (HI, wt %), and melt flow rate of the resulting polymer were measured. The melt flow rate was indicated by the melt flow index (MI, g-pp/10 minutes) according to ASTM. The molecular weight distribution of the polymer was measured. The results are shown in Table 1.

The catalyst activity indicating the amount of the formed polymer (F) g per 1 g of solid catalyst component per one hour of polymerization was calculated by the following formula.

Catalyst activity=formed polymer ($F$) g/solid catalyst component g/one hour

The polymer was continuously extracted with boiled n-heptane for six hours. An n-heptane-insoluble polymer (G) was dried and the weight was measured. The ratio of the heptane insoluble (HI, wt %) in the polymer was calculated by the following formula.

$HI$(wt %)=($G$)g/($F$)g×100

A melt index (MI) indicating the melt flow rate of the polymer was measured according to ASTEM D 1238 and JIS K 7210.

A molecular weight distribution of the polymer was evaluated by the ratio of Mw/Mn, a weight average molecular weight (Mw) and a number average molecular weight (Mn) measured under the following conditions using cross fractionation chromatography (CFC) ("CFC T-150B" manufactured by Mitsubishi Chemical Corporation).
Solvent: o-dichlorobenzene (ODCB)
Temperature: 140° C. (SEC)
Column: Shodex GPC UT-806M
Concentration of sample: 4 g/liter-ODCB (200 mg/50 ml-ODCB)
Amount added: 0.5 ml
Flow rate: 1.0 ml/min
Measured range: 0 to 140° C.

Example 8

The same experiment as in Example 7 was carried out, except for using (di-t-butylamino)(t-butylamino)(methylamino)methoxysilane obtained in Example 2 instead of bis (perhydroisoquinolino)(methylamino)methoxysilane. The results are shown in Table 1.

Example 9

The same experiment as in Example 7 was carried out, except for using (perhydroisoquinolino)(methylamino)ethylmethoxysilane obtained in Example 3 instead of bis(perhydroisoquinolino)(methylamino)methoxysilane. The results are shown in Table 1.

Example 10

The same experiment as in Example 7 was carried out, except for using bis(perhydroisoquinolino)(ethylamino) methoxysilane obtained in Example 4 instead of bis(perhydroisoquinolino)(methylamino)methoxysilane. The results are shown in Table 1.

Example 11

The same experiment as in Example 7 was carried out, except for using bis(ethylamino)(diethylamino)ethoxysilane obtained in Example 5 instead of bis(perhydroisoquinolino) (methylamino)methoxysilane. The results are shown in Table 1.

Example 12

The same experiment as in Example 7 was carried out, except for using (di-t-butylamino)(ethylamino)diethoxysilane obtained in Example 6 instead of bis(perhydroisoquinolino)(methylamino)methoxysilane. The results are shown in Table 1.

Example 13

Preparation of Solid Catalyst Component 2

A 500 ml round bottom flask equipped with a stirrer, of which the internal atmosphere had been sufficiently replaced with nitrogen gas, was charged with 4.76 g of anhydrous magnesium chloride, 25 ml of decane, and 23.4 ml of 2-ethylhexyl alcohol. The mixture was reacted at 130° C. for two hours, thereby obtaining a homogeneous solution. 1.11 g of phthalic acid anhydride was added to the homogeneous solution and reacted at 130° C. for one hour. The resulting reaction solution was added dropwise over one hour to 200 ml of titanium tetrachloride maintained at −20° C. in another 500 ml round bottom flask equipped with a stirrer, of which the internal atmosphere had been sufficiently replaced with nitrogen gas. After heating the solution to 110° C. over four hours, 2.68 ml of diisobutyl phthalate was added and reacted for two hours. After the reaction, the liquid was removed by filtration and the solid was washed with decane and hexane at 110° C. until no free titanium compound is detected. The solid was then filtered and dried, thereby obtaining a solid catalyst component in a form of a powder. The content of titanium in the solid catalyst component was measured and found to be 3.1 wt %.

Preparation of Polymerization Catalyst and Polymerization

A catalyst for polymerization was prepared and polymerization was carried out in the same manner as in Example 7, except for using the solid catalyst component 2 obtained above instead of the solid catalyst component 1. The results are shown in Table 1.

Example 14

Preparation of Solid Catalyst Component 3

A 1,000 ml round bottom flask equipped with a stirrer, of which the internal atmosphere had been sufficiently replaced with nitrogen gas, was charged with 32 g of magnesium turnings for Grignard reagent. A mixed solution containing 120 g of butylchloride and 500 ml of dibutyl ether was added dropwise to the magnesium at 50° C. over four hours and reacted at 60° C. for one hour. After the reaction, the solution was cooled to room temperature, and the solid was removed by filtration to obtain a magnesium compound solution. A 500 ml round bottom flask equipped with a stirrer, of which the internal atmosphere had been sufficiently replaced with nitrogen gas, was charged with 240 ml of hexane, 5.4 g of tetrabuthoxytitanium, and 61.4 g of tetraethoxysilane to obtain a homogeneous solution. 150 ml of the magnesium compound solution was added dropwise to the homogeneous solution and reacted at 5° C. for four hours. The mixture was then stirred at room temperature for one hour. The resulting reaction mixture was filtered at room temperature to remove the liquid. The solid was washed eight times with 240 ml of hexane, and dried under reduced pressure to obtain a solid product. 8.6 g of the solid product was put into a 100 ml round bottom flask equipped with a stirrer, of which the internal atmosphere had been sufficiently replaced with nitrogen gas. 48 ml of toluene and 5.8 ml of diisobutyl phthalate were further added and reacted at 95° C. for one hour. After removing the liquid by filtration, the solid was washed eight times with 85 ml of toluene. After washing, a flask was charged with 21 ml of toluene, 0.48 ml of diisobutyl phthalate, and 12.8 ml of titanium tetrachloride. The mixture was reacted at 95° C. for eight hours. After the reaction, the liquid was separated from the solid at 95° C. The solid was washed twice with 48 ml of toluene, and the above-mentioned treatment with the mixture of diisobutyl phthalate and titanium tetrachloride was repeated in the same manner. The resulting solid was then washed eight times with 48 ml of hexane, filtered, and dried, thereby obtaining a solid catalyst component in a form of a powder. The content of titanium in the solid catalyst component was measured and found to be 2.1 wt %.

<Preparation of Polymerization Catalyst and Polymerization>

A catalyst for polymerization was prepared and polymerization was carried out in the same manner as in Example 7, except for using the solid catalyst component 3 obtained above instead of the solid catalyst component 1. The results are shown in Table 1.

COMPARATIVE EXAMPLE 1

A solid catalyst component was prepared and polymerization was carried out in the same manner as in Example 7, except for using cyclohexylmethyldimethoxysilane instead of (perhydroisoquinolino)(methylamino)methoxysilane. The results are shown in Table 1.

COMPARATIVE EXAMPLE 2

A solid catalyst component was prepared and polymerization was carried out in the same manner as in Example 7, except for using bis(diethylamino)dimethoxysilane instead of (perhydroisoquinolino)(methylamino)methoxysilane. The results are shown in Table 1.

COMPARATIVE EXAMPLE 3

A solid catalyst component was prepared and polymerization was carried out in the same manner as in Example 7, except for using diisopropylaminotriethoxysilane instead of (perhydroisoquinolino)(methylamino)methoxysilane. The results are shown in Table 1.

COMPARATIVE EXAMPLE 4

A solid catalyst component was prepared and polymerization was carried out in the same manner as in Example 7, except for using tris(dimethylamino)methoxysilane instead of (perhydroisoquinolino)(methylamino)methoxysilane. The results are shown in Table 1.

TABLE 1

| | | Polymerization activity g-PP/g-cat. | HI wt % | BD g/ml | MI g/10 min | Mw/Mn |
|---|---|---|---|---|---|---|
| Example | 7 | 45,500 | 97.5 | 0.44 | 60 | 18 |
| | 8 | 58,600 | 98.2 | 0.44 | 100 | 15 |
| | 9 | 49,000 | 98.0 | 0.44 | 210 | — |
| | 10 | 48,800 | 97.3 | 0.44 | 180 | 17 |
| | 11 | 48,600 | 97.9 | 0.44 | 250 | — |
| | 12 | 46,800 | 97.5 | 0.44 | 180 | 15 |
| | 13 | 36,100 | 97.6 | 0.44 | 250 | — |
| | 14 | 48,900 | 98.1 | 0.44 | 190 | — |
| Comparative Example | 1 | 47,100 | 97.2 | 0.44 | 17 | 7.3 |
| | 2 | 16,500 | 94.4 | 0.44 | 199 | — |
| | 3 | 30,900 | 97.7 | 0.44 | 40 | — |
| | 4 | 15,300 | 90.3 | 0.43 | 79 | — |

Example 15

The same experiment as in Example 7 was carried out, except for using bis(diethylamino)(ethylamino)ethoxysilane instead of bis(perhydroisoquinolino)(methylamino)methoxysilane. The catalyst activity, heptane insoluble components (HI), and melt flow rate (MI) of the resulting polymer were measured. The results are shown in Table 2.

Example 16

The same experiment as in Example 7 was carried out, except for using bis(ethylamino)(diphenylamino)ethoxysilane instead of bis(perhydroisoquinolino)(methylamino) methoxysilane. The results are shown in Table 2.

Example 17

The same experiment as in Example 7 was carried out, except for using (ethylamino)(diethylamino)methoxyvinylsilane instead of bis(perhydroisoquinolino)(methylamino) methoxysilane. The results are shown in Table 2.

Example 18

The same experiment as in Example 7 was carried out, except for using (ethylamino)(dimethylamino)(ethoxy)cyclopentylsilane instead of bis(perhydroisoquinolino)(methylamino)methoxysilane. The results are shown in Table 2.

Example 19

The same experiment as in Example 7 was carried out, except for using (ethylamino)(diethylamino)(ethoxy)isopropylsilane instead of bis(perhydroisoquinolino)(methylamino)methoxysilane. The results are shown in Table 2.

Example 20

The same experiment as in Example 7 was carried out, except for using (ethylamino)(dimethylamino)(methoxy) thexylsilane instead of bis(perhydroisoquinolino)(methylamino)methoxysilane. The results are shown in Table 2.

Example 21

The same experiment as in Example 7 was carried out, except for using (ethylamino)(dimethylamino)(ethoxy)vinylsilane instead of bis(perhydroisoquinolino)(methylamino)methoxysilane. The results are shown in Table 2.

Example 22

The same experiment as in Example 7 was carried out, except for using (cyclopentylamino)(diphenylamino)dimethoxysilane instead of bis(perhydroisoquinolino)(methylamino)methoxysilane. The results are shown in Table 2.

Example 23

The same experiment as in Example 7 was carried out, except for using (benzylamino)(diisopropylamino)diethoxysilane instead of bis(perhydroisoquinolino)(methylamino)methoxysilane. The results are shown in Table 2.

Example 24

The same experiment as in Example 7 was carried out, except for using bis(diethylamino)(ethylamino)n-butoxysilane instead of bis(perhydroisoquinolino)(methylamino)methoxysilane. The results are shown in Table 2.

Example 25

The same experiment as in Example 7 was carried out, except for using (ethylamino)(dimethylamino)(ethoxy)p-methoxyphenylsilane instead of bis(perhydroisoquinolino)(methylamino)methoxysilane. The results are shown in Table 2.

TABLE 2

|  |  | Polymerization activity g-PP/g-cat. | HI wt % | MI g/10 min |
|---|---|---|---|---|
| Example | 15 | 35,000 | 95.8 | 150 |
|  | 16 | 40,100 | 94.3 | 250 |
|  | 17 | 30,000 | 96.4 | 52 |
|  | 18 | 31,000 | 96.2 | 160 |
|  | 19 | 30,500 | 96.1 | 170 |
|  | 20 | 41,000 | 96.5 | 43 |
|  | 21 | 36,000 | 95.7 | 150 |
|  | 22 | 37,000 | 97.2 | 25 |
|  | 23 | 32,000 | 92.1 | 160 |
|  | 24 | 35,000 | 92.6 | 165 |
|  | 25 | 28,000 | 93.5 | 140 |

Example 26

Synthesis of Aminosilane Compound 7

Tetrakis(ethylamino)silane was synthesized by a common method by reacting silicon tetrachloride and ethylamine in an amount of ten times mol of silicon tetrachloride in a toluene solvent. A three-necked flask of which the internal atmosphere was sufficiently replaced with nitrogen gas was charged with 60 ml of a THF solution containing 0.05 mol of tetrakis(ethylamino)silane. The solution was cooled to −10° C. while stirring. 30 ml of a THF solution containing 0.05 mol of methyl alcohol was slowly added dropwise to the THF solution containing 0.05 mol of tetrakis(ethylamino)silane using a dripping funnel. After the addition, the mixture was heated to 40° C. and reacted for three hours. The solvent of the reaction mixture was evaporated under reduced pressure and the main product of tris(ethylamino)methoxysilane was purified by distillation under reduced pressure. As a result of elementary analysis, the compound was found to consist of C, 43.79% (43.94%), H, 11.01% (11.06%), N, 21.90% (21.96%), wherein the percentages in the parentheses are theoretical values.

Example 27

Synthesis of Aminosilane Compound 8

Tetrakis(isopropylamino)silane was synthesized according to the appropriate method by reacting silicon tetrachloride and isopropylamine in an amount of ten times mol of silicon tetrachloride in a toluene solvent. A three-necked flask of which the internal atmosphere was sufficiently replaced with nitrogen gas was charged with 60 ml of a THF solution containing 0.05 mol of tetrakis(isopropylamino)silane. The solution was cooled to −10° C. while stirring. 30 ml of a THF solution containing 0.05 mol of ethyl alcohol was slowly added dropwise to the THF solution containing 0.05 mol of tetrakis(isopropylamino)silane using a dripping funnel. After the addition, the mixture was heated to 40° C. and reacted for two hours. The solvent and the like of the reaction mixture was evaporated under reduced pressure and the main product of tris(isopropylamino)ethoxysilane was purified by distillation under reduced pressure. As a result of elementary analysis, the compound obtained was found to consist of C, 53.35% (53.39%), H, 11.78% (11.81%), N, 16.92% (16.98%), wherein the percentages in the parentheses are theoretical values.

Example 28

Synthesis of Aminosilane Compound 9

Tetrakis(cyclopentylamino)silane was synthesized by a common method by reacting silicon tetrachloride with cyclopentylamine and dimethylaniline in amounts respectively of four times and five times mol of silicon tetrachloride in a toluene solvent. A three-necked flask of which the internal atmosphere was sufficiently replaced with nitrogen gas was charged with 60 ml of a THF solution containing 0.05 mol of tetrakis(cyclopentylamino)silane. The solution was cooled to −10° C. while stirring. 30 ml of a THF solution containing 0.05 mol of methyl alcohol was slowly added dropwise to the THF solution containing 0.05 mol of tetrakis(cyclopentylamino)silane using a dripping funnel. After the addition, the mixture was heated to 40° C. and reacted for three hours. The solvent and the like of the reaction mixture was evaporated under reduced pressure and the main product of tris(cyclopentylamino)methoxysilane was purified by distillation under reduced pressure. As a result of elementary analysis, the compound obtained was found to consist of C, 61.55% (61.68%), H, 10.70% (10.68%), N, 13.42% (13.49%), wherein the percentages in the parentheses are theoretical values.

Example 29

Synthesis of Aminosilane Compound 10

Tetrakis(cyclohexylamino)silane was synthesized by a common method by reacting silicon tetrachloride and cyclohexylamine in an amount ten times mol of silicon tetrachloride in a toluene solvent and purified by a recrystallization method. A three-necked flask of which the internal atmosphere was sufficiently replaced with nitrogen gas was charged with 60 ml of a THF solution containing 0.05 mol of tetrakis(cyclohexylamino)silane. The solution was cooled to −10° C. while stirring. 30 ml of a THF solution containing 0.05 mol of methyl alcohol was slowly added dropwise to the THF solution containing 0.05 mol of tetrakis(cyclohexylamino)silane using a dripping funnel. After the addition, the mixture was heated to 40° C. and reacted for three hours. The solvent and the like of the reacted mixture were evaporated under reduced pressure and the main product of tris(cyclohexylamino)methoxysilane was purified by distillation under reduced pressure. As a result of elementary analysis, the compound was found to consist of C, 64.45% (64.53%), H, 11.10% (11.12%), N, 11.86% (11.88%), wherein the percentages in the parentheses are theoretical values.

Example 30

Synthesis of Aminosilane Compound 11

A three-necked flask of which the internal atmosphere was sufficiently purged with nitrogen gas was charged with 80 ml of a toluene solution containing 0.12 mol of t-butylamine. The solution was cooled to −10° C. while stirring. 60 ml of a THE solution containing 0.12 mol of n-BuMgCl was slowly added to the solution using a dripping funnel. After the addition, the mixture was reacted at 50° C. for one hour, thereby obtaining a slurry of a magnesium salt of t-butylamine. A three-necked flask of which the internal atmosphere was sufficiently purged with nitrogen gas was charged with a toluene solution containing 0.06 mol of tetramethoxysilane under a nitrogen gas atmosphere. The system was cooled to −10° C. while stirring. The above slurry of magnesium salt of t-butylamine was slowly added dropwise to the solution. After the addition, the mixture was gradually heated and reacted at 50° C. for three hours. A separately prepared solution of 30 ml of toluene containing 0.06 mol of methylamine was cooled to −10° C. 50 ml of a hexane solution containing 0.06 mol of BuLi which was prepared from a commercially available BuLi in a hexane solution was added dropwise to the toluene solution using a dripping funnel. The mixture was reacted at 40° C. for two hours to obtain a slurry of lithium salt of methylamine. The slurry was added dropwise to the above reaction mixture cooled to −10° C. mentioned above. After the addition, the mixture was reacted at 50° C. for three hours. The solid was separated from the solution by centrifugation in a nitrogen stream and washed with 20 ml of toluene. The washing solution was added to the solution. The solvent and the like were evaporated under reduced pressure and the main product of bis(t-butylamino)(methylamino)methoxysilane was purified by distillation under reduced pressure. As a result of elementary analysis, the compound was found to consist of C, 51.42% (51.45%), H, 11.61% (11.66%), N, 17.89% (18.00%), wherein the percentages in the parentheses are theoretical values.

Example 31

Synthesis of Aminosilane Compound 12

A three-necked flask of which the internal atmosphere was sufficiently purged with nitrogen gas was charged with 40 ml of a toluene solution containing 0.06 mol of t-butylamine. The solution was cooled to −10° C. while stirring. 60 ml of a THE solution containing 0.06 mol of n-BuMgCl was slowly added to the solution using a dripping funnel. After the addition, the mixture was reacted at 50° C. for one hour, thereby obtaining a slurry of a magnesium salt of t-butylamine. A three-necked flask of which the internal atmosphere was sufficiently purged with nitrogen gas was charged with a toluene solution containing 0.06 mol of tetramethoxysilane under a nitrogen gas atmosphere. The system was cooled to −10° C. while stirring. The slurry of a magnesium salt of t-butylamine was slowly added dropwise to the solution. After the addition, the mixture was gradually heated and reacted at 50° C. for two hours. This reacted mixture is referred to as reaction mixture (1). In a separate flask, 30 ml of toluene containing 0.06 mol of methylamine was cooled to −10° C. 50 ml of a hexane solution containing 0.06 mol of BuLi, prepared from a commercially available hexane solution of BuLi was added dropwise using a dripping funnel. The mixture was reacted at 40° C. for two hours to obtain a slurry of lithium salt of methylamine. The slurry was added dropwise to the reaction mixture (1) cooled to −10° C. mentioned above. After the addition, the mixture was reacted at 50° C. for three hours. This reacted mixture is referred to as reaction mixture (2). 30 ml of toluene containing 0.06 mol of ethylamine was cooled to −10° C. 50 ml of a hexane solution containing 0.06 mol of BuLi which was prepared from a commercially available hexane solution of BuLi was added dropwise using a dripping funnel. The mixture was reacted at 40° C. for two hours. A slurry of lithium salt of ethylamine was added dropwise to the system which is the reaction mixture (2) cooled to −10° C. mentioned above. After the addition, the mixture was reacted at 50° C. for three hours. The solid was separated from the solution by centrifugation in a nitrogen stream and washed twice with 20 ml of toluene. The washing liquid was added to the solution. The solvent and the like were evaporated under reduced pressure and the main product of (t-butylamino)(methylamino)(ethylamino)methoxysilane was purified by distillation under reduced pressure. As a result of elementary analysis, the compound was found to consist of C, 46.76% (46.79%), H, 11.23% (11.29%), N, 20.35% (20.46%), wherein the percentages in the parentheses are theoretical values.

Example 32

Synthesis of Aminosilane Compound 13

A three-necked flask of which the internal atmosphere was sufficiently purged with nitrogen gas was charged with 80 ml of a toluene solution containing 0.12 mol of cyclohexylamine. The solution was cooled to −10° C. while stirring. 60 ml of a THE solution containing 0.12 mol of n-BuMgCl was slowly added to the solution using a dripping funnel. After the addition, the mixture was reacted at 50° C. for one hour, thereby obtaining a slurry of magnesium salt of cyclohexylamine. A three-necked flask of which the internal atmosphere was sufficiently purged with nitrogen gas was charged with a toluene solution containing 0.06 mol of tetraethoxysilane under a nitrogen gas atmosphere. The system was cooled to −10° C. while stirring. The slurry of magnesium salt of cyclohexylamine was slowly added dropwise to the solution. After the addition, the mixture was gradually heated and reacted at 50° C. for three hours. Separately, 30 ml of toluene containing 0.06 mol of ethylamine was cooled to −10° C. 50 ml of a hexane solution containing 0.06 mol of BuLi which was prepared from a commercially available hexane solution of BuLi was added dropwise using a dripping funnel. The mixture was reacted at 40° C. for two hours to obtain a slurry of lithium salt of ethylamine. The slurry was added dropwise to the above-mentioned reaction mixture cooled to −10° C. After the addition, the mixture was reacted at 50° C. for three hours. The solid was separated from the solution by centrifugation in a nitrogen stream and washed twice with 20 ml of toluene. The washing liquid was added to the solution. The solvent and the like were evaporated under reduced pressure and the main product of bis(cyclohexylamino)(ethylamino) ethoxysilane was purified by distillation under reduced pressure. As a result of elementary analysis, the compound was found to consist of C, 61.25% (61.29%), H, 11.10% (11.25%), N, 13.25% (13.40%), wherein the percentages in the parentheses are theoretical values.

Example 33

Synthesis of Aminosilane Compound 14

A three-necked flask of which the internal atmosphere was sufficiently purged with nitrogen gas was charged with 80 ml of a toluene solution containing 0.14 mol of isobutylamine. The solution was cooled to −10° C. while stirring. 60 ml of a THE solution containing 0.14 mol of n-BuMgCl was slowly added to the solution using a dripping funnel. After the addition, the mixture was reacted at 50° C. for one hour, thereby obtaining a slurry of magnesium salt of isobutylamine. A three-necked flask of which the internal atmosphere was sufficiently purged with nitrogen gas was charged with a toluene solution containing 0.07 mol of tetra-n-propoxysilane under a nitrogen gas atmosphere. The system was cooled to −10° C. while stirring. The slurry of magnesium salt of isobutylamine was slowly added dropwise to the solution. After the addition, the mixture was gradually heated and reacted at 50° C. for three hours. Separately, 30 ml of toluene containing 0.07 mol of methylamine was cooled to −10° C. 50 ml of a hexane solution containing 0.07 mol of BuLi which was prepared from a commercially available hexane solution of BuLi was added dropwise using a dripping funnel. The mixture was reacted at 40° C. for two hours to obtain a slurry of lithium salt of methylamine. The slurry was added dropwise to the system which is the above mentioned mixture cooled to −10° C. After the addition, the mixture was reacted at 50° C. for three hours. The solid was separated from the solution by centrifugation in a nitrogen stream and washed twice with 20 ml of toluene. The washing liquid was added to the solution. The solvent and the like were evaporated under reduced pressure and the main product of bis(isobutylamino)(ethylamino)propoxysilane was purified by distillation under reduced pressure. As a result of elementary analysis, the compound was found to consist of C, 55.10% (55.12%), H, 11.92% (11.95%), N, 16.01% (16.07%), wherein the percentages in the parentheses are theoretical values.

Example 34

Preparation of Polymerization Catalyst and Polymerization

The same experiment as in Example 7 was carried out, except for using 0.13 mmol of tris(ethylamino)methoxysilane obtained in Example 26 instead of 0.13 mmol of bis(perhydroisoquinolino)(methylamino)methoxysilane. The results are shown in Table 3.

Example 35

The same experiment as in Example 34 was carried out, except for using tris(isopropylamino)ethoxysilane obtained in Example 27 instead of tris(ethylamino)methoxysilane. The results are shown in Table 3.

Example 36

The same experiment as in Example 34 was carried out, except for using tris(cyclopentylamino)methoxysilane obtained in Example 28 instead of tris(ethylamino)methoxysilane. The results are shown in Table 3.

Example 37

The same experiment as in Example 34 was carried out, except for using tris(cyclohexylamino)methoxysilane obtained in Example 29 instead of tris(ethylamino)methoxysilane. The results are shown in Table 3.

Example 38

The same experiment as in Example 34 was carried out, except for using bis(t-butylamino)(methylamino)methoxysilane obtained in Example 30 instead of tris(ethylamino)methoxysilane. The results are shown in Table 3.

Example 39

The same experiment as in Example 34 was carried out, except for using (t-butylamino)(methylamino)(ethylamino)methoxysilane obtained in Example 31 instead of tris(ethylamino)methoxysilane. The results are shown in Table 3.

Example 40

The same experiment as in Example 34 was carried out, except for using bis(cyclohexylamino)(ethylamino)ethoxysilane obtained in Example 32 instead of tris(ethylamino)methoxysilane. The results are shown in Table 3.

Example 41

The same experiment as in Example 34 was carried out, except for using bis(isobutylamino)(methylamino)propoxysilane obtained in Example 33 instead of tris(ethylamino)methoxysilane. The results are shown in Table 3.

Example 42

Preparation of Polymerization Catalyst and Polymerization

A catalyst for polymerization was prepared and polymerization as carried out in the same manner as in Example 34, except for using the solid catalyst component 2 obtained above instead of the solid catalyst component 1. The results are shown in Table 3.

Example 43

Preparation of Polymerization Catalyst and Polymerization

A catalyst for polymerization was prepared and the polymerization as carried out in the same manner as in Example 34, except for using the solid catalyst component 3 obtained above instead of the solid catalyst component 1. The results are shown in Table 3.

TABLE 3

| Example | | Polymerization activity g-PP/g-cat. | HI wt % | BD g/ml | MI g/10 min | Mw/Mn |
|---|---|---|---|---|---|---|
| Example | 34 | 39,200 | 97.5 | 0.44 | 220 | — |
| | 35 | 41,600 | 96.2 | 0.44 | 280 | — |

TABLE 3-continued

| | Polymerization activity g-PP/g-cat. | HI wt % | BD g/ml | MI g/10 min | Mw/Mn |
|---|---|---|---|---|---|
| 36 | 46,000 | 95.5 | 0.44 | 320 | — |
| 37 | 47,800 | 95.1 | 0.44 | 520 | — |
| 38 | 57,100 | 97.5 | 0.44 | 172 | — |
| 39 | 46,100 | 96.5 | 0.44 | 189 | — |
| 40 | 36,100 | 97.0 | 0.44 | 200 | — |
| 41 | 51,000 | 96.8 | 0.44 | 174 | — |
| 42 | 20,500 | 96.2 | 0.43 | 230 | — |
| 43 | 40,200 | 96.4 | 0.45 | 220 | — |

Example 44

Synthesis of Aminosilane Compound 15

A flask of which the internal atmosphere was sufficiently replaced with nitrogen gas was charged with 60 ml of a THE solution containing 0.05 mol of methylamine. The solution was cooled to −10° C. while stirring. 60 ml of a hexane solution containing 0.05 mol of BuLi was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.05 mol of dicyclopentyldimethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for two hours. After the reaction, the solid was separated from the liquid by centrifugation in a nitrogen stream and washed twice with 10 ml of toluene. The washing liquid was added to the solution. The solvent was evaporated under reduced pressure and the main product of dicyclopentyl(methylamino)methoxysilane was purified by distillation under reduced pressure. As a result of elementary analysis, the compound was found to consist of C, 63.34% (63.38%), H, 11.01% (11.08%), N, 6.10% (6.16%), wherein the percentages in the parentheses are theoretical values.

Example 45

Synthesis of Aminosilane Compound 16

A flask of which the internal atmosphere was sufficiently replaced with nitrogen gas was charged with 60 ml of a THF solution containing 0.06 mol of methylamine. The solution was cooled to −10° C. while stirring. 60 ml of a THF solution containing 0.06 mol of BuMgCl was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.06 mol of diisopropyldiethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for two hours. After the reaction, the solid was separated from the liquid by centrifugation in a nitrogen stream and washed twice with 10 ml of toluene. The washing liquid was added to the solution. The solvent was evaporated under reduced pressure and the main product of diisopropyl(methylamino)ethoxysilane was purified by distillation under reduced pressure. As a result of elementary analysis, the compound was found to consist of C, 57.03% (57.08%), H, 12.18% (12.24%), N, 7.34% (7.40%), wherein the percentages in the parentheses are theoretical values.

Example 46

Synthesis of Aminosilane Compound 17

A flask of which the internal atmosphere was sufficiently replaced with nitrogen gas was charged with 60 ml of a THF solution containing 0.05 mol of ethylamine. The solution was cooled to −10° C. while stirring. 60 ml of a hexane solution containing 0.05 mol of BuLi was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.05 mol of cyclohexylmethyldiethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for two hours. After the reaction, the solid was separated from the liquid by centrifugation in a nitrogen stream and washed twice with 10 ml of toluene. The washing liquid was added to the solution. The solvent was evaporated under reduced pressure and the main product of cyclohexylmethyl(ethylamino)ethoxysilane was purified by distillation under reduced pressure. As a result of elementary analysis, the compound was found to consist of C, 61.23% (61.33%), H, 11.63% (11.70%), N, 6.44% (6.50%), wherein the percentages in the parentheses are theoretical values.

Example 47

Synthesis of Aminosilane Compound 18

A flask of which the internal atmosphere was sufficiently replaced with nitrogen gas was charged with 60 ml of a THF solution containing 0.05 mol of methylamine. The solution was cooled to −10° C. while stirring. 60 ml of a THF solution containing 0.05 mol of BuMgCl was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.05 mol of cyclohexylmethyldimethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for two hours. After the reaction, the solid was separated from the liquid by centrifugation in a nitrogen stream and washed twice with 10 ml of toluene. The washing liquid was added to the solution. The solvent was evaporated under reduced pressure and the main product of cyclohexylmethyl(methylamino)methoxysilane was purified by distillation under reduced pressure. As a result of elementary analysis, the compound was found to consist of C, 57.65% (57.70%), H, 11.10% (11.30%), N, 7.44% (7.48%), wherein the percentages in the parentheses are theoretical values.

Example 48

Synthesis of Aminosilane Compound 19

A flask of which the internal atmosphere was sufficiently replaced with nitrogen gas was charged with 60 ml of a THF solution containing 0.06 mol of methylamine. The solution was cooled to −10° C. while stirring. 60 ml of a hexane solution containing 0.06 mol of BuLi was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.06 mol of t-butylethyldimethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for two hours. After the reaction, the solid was separated from the liquid by centrifugation in a nitrogen stream and washed twice with 10 ml of toluene. The washing liquid was added to the solution. The solvent was evaporated under reduced pressure and the main product of t-butylethyl(methylamino)methoxysilane was purified by distillation under reduced pressure. The solvent and the like were evaporated under reduced pressure and the main product of t-butylethyl(methylamino)methoxysilane was purified by distillation under reduced pressure. As a result of elementary analysis, the compound was found to consist of C, 54.73% (54.80%), H, 12.00% (12.07%), N, 7.92% (7.99%), wherein the percentages in the parentheses are theoretical values.

Example 49

Synthesis of Aminosilane Compound 20

A flask of which the internal atmosphere was sufficiently replaced with nitrogen gas was charged with 60 ml of a THF solution containing 0.05 mol of ethylamine. The solution was cooled to −10° C. while stirring. 60 ml of a hexane solution containing 0.05 mol of BuLi was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.05 mol of t-butylmethyldiethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for two hours. After the reaction, the solid was separated from the liquid by centrifugation in a nitrogen stream and washed twice with 10 ml of toluene. The washing liquid was added to the solution. The solvent was evaporated under reduced pressure and the main product of t-butylmethyl(ethylamino)ethoxysilane was purified by distillation under reduced pressure. As a result of elementary analysis, the compound was found to consist of C: 56.98% (57.08%), H, 12.20% (12.24%), N, 7.35% (7.40%), wherein the percentages in the parentheses are theoretical values.

Example 50

Synthesis of Aminosilane Compound 21

A flask of which the internal atmosphere was sufficiently replaced with nitrogen gas was charged with 60 ml of a THF solution containing 0.05 mol of ethylamine. The solution was cooled to −10° C. while stirring. 60 ml of a hexane solution containing 0.05 mol of BuLi was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.05 mol of dicyclohexyldimethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for two hours. After the reaction, the solid was separated from the liquid by centrifugation in a nitrogen stream and washed twice with 10 ml of toluene. The washing liquid was added to the solution. The solvent was evaporated under reduced pressure and the main product of dicyclohexyl(ethylamino)methoxysilane was purified by distillation under reduced pressure. As a result of elementary analysis, the compound was found to consist of C, 66.65% (66.85%), H, 11.47% (11.59%), N, 5.12% (5.20%), wherein the percentages in the parentheses are theoretical values.

Example 51

Synthesis of Aminosilane Compound 22

A flask of which the internal atmosphere was sufficiently replaced with nitrogen gas was charged with 60 ml of a THF solution containing 0.06 mol of methylamine. The solution was cooled to −10° C. while stirring. 60 ml of a hexane solution containing 0.06 mol of BuLi was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.06 mol of di-t-butyldimethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for two hours. After the reaction, the solid was separated from the liquid by centrifugation in a nitrogen stream and washed twice with 10 ml of toluene. The washing liquid was added to the solution. The solvent was evaporated under reduced pressure and the main product of di-t-butyl(methylamino)methoxysilane was purified by distillation under reduced pressure. As a result of elementary analysis, the compound was found to consist of C, 59.00% (59.05%), H, 12.30% (12.39%), N, 6.81% (6.89%), wherein the percentages in the parentheses are theoretical values.

Example 52

Synthesis of Aminosilane Compound 23

A flask of which the internal atmosphere was sufficiently replaced with nitrogen gas was charged with 60 ml of a THF solution containing 0.05 mol of n-propylamine. The solution was cooled to −10° C. while stirring. 60 ml of a hexane solution containing 0.05 mol of BuLi was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.05 mol of diisopropyldimethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for three hours. After the reaction, the solid was separated from the liquid by centrifugation in a nitrogen stream and washed twice with 10 ml of toluene. The washing liquid was added to the solution. The solvent was evaporated under reduced pressure and the main product of diisopropyl(n-propylamino)methoxysilane was purified by distillation under reduced pressure. As a result of elementary analysis, the compound was found to consist of C, 59.00% (59.05%), H, 12.23% (12.39%), N, 6.61% (6.89%), wherein the percentages in the parentheses are theoretical values.

Example 53

Synthesis of Aminosilane Compound 24

A flask of which the internal atmosphere was sufficiently replaced with nitrogen gas was charged with 60 ml of a THF solution containing 0.06 mol of methylamine. The solution was cooled to −10° C. while stirring. 60 ml of a THF solution containing 0.06 mol of BuMgCl was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.06 mol of phenylmethyldimethoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for two hours. After the reaction, the solid was separated from the liquid by centrifugation in a nitrogen stream and washed twice with 10 ml of toluene. The washing liquid was added to the solution. The solvent was evaporated under reduced pressure and the main product of phenylmethyl(methylamino)methoxysilane was purified by distillation under reduced pressure. As a result of elementary analysis, the compound was found to consist of C, 59.59% (59.62%), H, 8.41% (8.34%), N, 7.61% (7.73%), wherein the percentages in the parentheses are theoretical values.

Example 54

Synthesis of Aminosilane Compound 25

A flask of which the internal atmosphere was sufficiently replaced with nitrogen gas was charged with 60 ml of a THF solution containing 0.05 mol of ethylamine. The solution was cooled to −10° C. while stirring. 60 ml of a hexane solution containing 0.05 mol of BuLi was slowly added to the solution in a nitrogen stream using a dripping funnel. After the addition, the mixture was gradually heated and reacted at 50° C. for two hours. Another flask of which the internal atmosphere was purged with nitrogen gas was charged with 60 ml of a toluene solution containing 0.05 mol of diisopropyldi-n-propoxysilane in a nitrogen stream. The solution was cooled to −10° C. while stirring. All the slurry of the reaction mixture synthesized above was slowly added to the toluene solution using a dripping funnel. After the addition, the mixture was gradually heated and reacted at 50° C. for three hours. After the reaction, the solid was separated from the liquid by centrifugation in a nitrogen stream and washed twice with 10 ml of toluene. The washing liquid was added to the solution. The solvent was evaporated under reduced pressure and the main product of diisopropyl(ethylamino)n-propoxysilane was purified by distillation under reduced pressure. As a result of elementary analysis, the compound was found to consist of C, 60.57% (60.77%), H, 12.43% (12.52%), N, 6.32% (6.44%), wherein the percentages in the parentheses are theoretical values.

Example 55

The same experiment as in Example 34 was carried out, except for using dicyclopentyl(ethylamino)methoxysilane obtained in Example 44 instead of tris(ethylamino)methoxysilane. The results are shown in Table 4.

Example 56

The same experiment as in Example 34 was carried out, except for using diisopropyl(methylamino)ethoxysilane obtained in Example 45 instead of tris(ethylamino)methoxysilane. The results are shown in Table 4.

Example 57

The same experiment as in Example 34 was carried out, except for using cyclohexylmethyl(ethylamino)ethoxysilane obtained in Example 46 instead of tris(ethylamino)methoxysilane. The results are shown in Table 4.

Example 58

The same experiment as in Example 34 was carried out, except for using cyclohexylmethyl(methylamino)methoxysilane obtained in Example 47 instead of tris(ethylamino)methoxysilane. The results are shown in Table 4.

Example 59

The same experiment as in Example 34 was carried out, except for using t-butylethyl(methylamino)methoxysilane obtained in Example 48 instead of tris(ethylamino)methoxysilane. The results are shown in Table 4.

Example 60

The same experiment as in Example 34 was carried out, except for using t-butylmethyl(ethylamino)ethoxysilane obtained in Example 49 instead of tris(ethylamino)methoxysilane. The results are shown in Table 4.

Example 61

The same experiment as in Example 34 was carried out, except for using dicyclohexyl(ethylamino)methoxysilane obtained in Example 50 instead of tris(ethylamino)methoxysilane. The results are shown in Table 4.

Example 62

The same experiment as in Example 34 was carried out, except for using di-t-butyl(methylamino)methoxysilane obtained in Example 51 instead of tris(ethylamino)methoxysilane. The results are shown in Table 4.

Example 63

The same experiment as in Example 34 was carried out, except for using diisopropyl(n-propylamino)methoxysilane obtained in Example 52 instead of tris(ethylamino)methoxysilane. The results are shown in Table 4.

Example 64

The same experiment as in Example 34 was carried out, except for using phenylmethyl(methylamino)methoxysilane obtained in Example 53 instead of tris(ethylamino)methoxysilane. The results are shown in Table 4.

Example 65

The same experiment as in Example 34 was carried out, except for using diisopropyl(ethylamino)n-propoxysilane obtained in Example 54 instead of tris(ethylamino)methoxysilane. The results are shown in Table 4.

Example 66

A catalyst for polymerization was prepared and polymerization was carried out in the same manner as in Example 55, except for using the solid catalyst component 2 obtained in Example 13 instead of the solid catalyst component 1. The results are shown in Table 4.

Example 67

A catalyst for polymerization was prepared and polymerization was carried out in the same manner as in Example 55, except for using the solid catalyst component 3 obtained in Example 14 instead of the solid catalyst component 1. The results are shown in Table 4.

TABLE 4

| | | Polymerization activity g-PP/g-cat. | HI wt % | BD g/ml | MI g/10 min | Mw/Mn |
|---|---|---|---|---|---|---|
| Example | 55 | 50,500 | 98.0 | 0.44 | 90 | — |
| | 56 | 48,600 | 97.8 | 0.44 | 120 | — |
| | 57 | 49,000 | 97.5 | 0.44 | 240 | — |
| | 58 | 52,800 | 95.1 | 0.44 | 96 | — |
| | 59 | 48,100 | 97.5 | 0.44 | 80 | — |
| | 60 | 45,800 | 97.5 | 0.44 | 180 | — |
| | 61 | 51,100 | 97.0 | 0.44 | 70 | — |
| | 62 | 48,900 | 98.1 | 0.44 | 90 | — |
| | 63 | 45,000 | 96.2 | 0.43 | 210 | — |
| | 64 | 48,200 | 97.4 | 0.45 | 96 | — |
| | 65 | 47,100 | 96.5 | 0.43 | 193 | — |
| | 66 | 21,500 | 97.2 | 0.44 | 230 | 7.3 |
| | 67 | 51,100 | 95.7 | 0.43 | 99 | — |

Example 68

The same experiment as in Example 34 was carried out, except for using p-methoxyphenylmethyl(ethylamino)ethoxysilane instead of tris(ethylamino)methoxysilane. The catalyst activity, heptane insoluble components (HI), and melt index (MI) of the resulting polymer were measured. The results are shown in Table 5.

Example 69

The same experiment as in Example 34 was carried out, except for using thexylmethyl(ethylamino)methoxysilane instead of tris(ethylamino)methoxysilane. The results are shown in Table 5.

Example 70

The same experiment as in Example 34 was carried out, except for using didecahydronaphthyl(ethylamino)methoxysilane instead of tris(ethylamino)methoxysilane. The results are shown in Table 5.

Example 71

The same experiment as in Example 34 was carried out, except for using tris(n-decylamino)methoxysilane instead of tris(ethylamino)methoxysilane. The results are shown in Table 5.

Example 72

The same experiment as in Example 34 was carried out, except for using (ethylamino)(methoxy)-2,5-dimethylsilacyclopentane instead of tris(ethylamino)methoxysilane. The results are shown in Table 5.

Example 73

The same experiment as in Example 34 was carried out, except for using (ethylamino)(ethoxy)-2,6-dimethylsilacyclohexane instead of tris(ethylamino)methoxysilane. The results are shown in Table 5.

Example 74

The same experiment as in Example 34 was carried out, except for using benzylethyl(ethylamino)ethoxysilane instead of tris(ethylamino)methoxysilane. The results are shown in Table 5.

Example 75

The same experiment as in Example 34 was carried out, except for using phenylvinyl(ethylamino)methoxysilane instead of tris(ethylamino)methoxysilane. The results are shown in Table 5.

Example 76

The same experiment as in Example 34 was carried out, except for using tris(ethylamino)t-butoxysilane instead of tris(ethylamino)methoxysilane. The results are shown in Table 5.

Example 77

The same experiment as in Example 34 was carried out, except for using tris(ethylamino)cyclohexoxysilane instead of tris(ethylamino)methoxysilane. The results are shown in Table 5.

TABLE 5

| | | Polymerization activity g-PP/g-cat. | HI wt % | MI g/10 min |
|---|---|---|---|---|
| Example | 68 | 32,000 | 96.2 | 78 |
| | 69 | 41,000 | 97.1 | 48 |
| | 70 | 27,000 | 96.3 | 45 |
| | 71 | 31,000 | 92.5 | 30 |
| | 72 | 42,000 | 97.8 | 52 |
| | 73 | 45,000 | 97.6 | 34 |
| | 74 | 36,000 | 96.3 | 85 |
| | 75 | 32,000 | 96.5 | 65 |

TABLE 5-continued

| | Polymerization activity g-PP/g-cat. | HI wt % | MI g/10 min |
|---|---|---|---|
| 76 | 26,000 | 94.8 | 120 |
| 77 | 32,000 | 95.1 | 128 |

From the above results, it is clear that polymerization of propylene in the presence of the catalyst containing the aminosilane compound as an external donor can produce a propylene polymer having high stereoregularity in a high yield and an excellent hydrogen response. Also, the molecular weight distribution of the resulting polymer can be broaden depending on the aminosilane compound.

INDUSTRIAL APPLICABILITY

A catalyst for polymerization of olefins of the present invention is capable of maintaining higher stereoregularity and yield of a polymer than the known catalyst and capable of producing olefin polymers having a high melt flow rate with a given amount of hydrogen (excellent hydrogen response). Therefore, the general polyolefins can be provided at low cost due to the reduced amount of hydrogen used during polymerization and the high catalyst activity. Also, the catalyst is expected to be useful for manufacturing high-functional olefin polymers.

The invention claimed is:

1. An aminosilane compound of formula (1), $$(R^1R^2N)_m(R^3HN)_nR^4_pSi(OR^5)_q \quad (1)$$

wherein m is an integer of 0, 1, or 2, n and q are integers of 1 to 3, and p is an integer of 0, 1, or 2, wherein m+n+p+q=4, when m=0, q=1 and p=3−n; $R^1$, $R^2$, and $R^3$ individually represent a linear or branched alkyl group having 1 to 20 carbon atoms, a cycloalkyl group or a derivative thereof, a vinyl group, an allyl group, or an aralkyl group, each of which may contain a heteroatom, wherein $R^1$ and $R^2$ may bond to form a ring; $R^4$ individually represents a linear or branched alkyl group having 1 to 20 carbon atoms, a cycloalkyl group or a derivative thereof, a vinyl group, an allyl group, or an aralkyl group, each of which may contain a heteroatom, and, when m=0, n=1, and q=1, two $R^4$s may bond to form a ring; and $R^5$ individually represents a linear or branched alkyl group having 1 to 12 carbon atoms, a cycloalkyl group or a derivative thereof, a vinyl group, an allyl group, or an aralkyl group, each of which may contain a heteroatom.

2. The aminosilane compound according to claim 1, wherein, in the formula (1), m=n=p=q=1.

3. The aminosilane compound according to claim 1, wherein, in the formula (1), m=0, n=1, p=2, and q=1.

4. The aminosilane compound according to claim 1, wherein, in the formula (1), m=0, n=2, p=1, and q=1.

5. The aminosilane compound according to claim 1, wherein, in the formula (1), m=0, n=3, p=0, and q=1.

6. The aminosilane compound according to claim 1, wherein, in the formula (1), m=1, n=1, p=0, and q=2.

7. The aminosilane compound according to claim 1, wherein, in the formula (1), m=1, n=2, p=0, and q=1.

8. The aminosilane compound according to claim 1, wherein, in the formula (1), m=2, n=1, p=0, and q=1.

9. A catalyst for olefin polymerization comprising the aminosilane compound according to claim 1.

10. A catalyst comprising:
(A) a solid catalyst component comprising magnesium, titanium, a halogen, and an electron donor compound,
(B) an organoaluminum compound of formula (2), $$R^6_pAlQ_{3-p} \quad (2)$$

wherein $R^6$ represents an alkyl group having 1 to 4 carbon atoms, Q represents a hydrogen atom or a halogen atom, and p represents a real number satisfying the formula 0<p≦3, and
(C) the aminosilane compound according to claim 1.

11. The catalyst according to claim 10, wherein component (A) is obtained by causing (a) a magnesium compound, (b) a tetravalent titanium halogen compound, and (c) an electron donor compound to come in contact with each other.

12. A process for producing an olefin polymer comprising polymerizing an olefin in the presence of the catalyst for olefin polymerization according to claim 9.

13. The process for producing an olefin polymer according to claim 12, wherein the olefin is propylene.

14. A process for producing an olefin polymer comprising polymerizing an olefin in the presence of the catalyst according to claim 10.

15. The process for producing an olefin polymer according to claim 14, wherein the olefin is propylene.

16. The aminosilane compound according to claim 1, selected from the group consisting of (perhydroisoquinolino)(methylamino)ethylmethoxysilane, (ethylamino)(diethylamino)(methoxy)vinylsilane, (ethylamino)(dimethylamino)(ethoxy)cyclopentylsilane, (ethylamino)(diethylamino)(ethoxy)isopropylsilane, (ethylamino)(dimethylamino)(methoxy)thexylsilane, (ethylamino)(dimethylamino)(ethoxy)vinylsilane, and (ethylamino)(diethylamino)(ethoxy)-p-methoxyphenylsilane.

17. The aminosilane compound according to claim 1, selected from the group consisting of dicyclopentyl(methylamino)methoxysilane, dicyclopentyl(ethylamino)methoxysilane, diisopropyl(methylamino)ethoxysilane, cyclohexylmethyl(ethylamino)ethoxysilane, cyclohexylmethyl(methylamino)methoxysilane, t-butylethyl(methylamino)methoxysilane, t-butylmethyl(ethylamino)ethoxysilane, t-butylmethyl(ethylamino)methoxysilane, dicyclohexyl(ethylamino)methoxysilane, di-t-butyl(methylamino)methoxysilane, diisopropyl(n-propylamino)methoxysilane, phenylmethyl(methylamino)methoxysilane, diisopropyl(ethylamino)n-propoxysilane, p-methoxyphenylmethyl(ethylamino)ethoxysilane, thexylmethyl(ethylamino)methoxysilane, didecahydronaphthyl(ethylamino)methoxysilane, tris(n-decylamino)methoxysilane, (ethylamino)(methoxy)-2,5-dimethylsilacyclopentane, (ethylamino)(methoxy)-2,6-dimethylsilacyclohexane, benzylethyl(ethylamino)ethoxysilane, and phenylvinyl(ethylamino)methoxysilane.

18. The aminosilane compound according to claim 1, selected from the group consisting of tris(ethylamino)methoxysilane, tris(isopropylamino)ethoxysilane, tris(cyclopentylamino)methoxysilane, tris(cyclohexylamino)methoxysilane, bis(t-butylamino)(methylamino)methoxysilane, (t-butylamino)(methylamino)(ethylamino)methoxysilane, bis(cyclohexylamino)(ethylamino)ethoxysilane, bis(isobutylamino)(methylamino)propoxysilane, tris(n-decylamino)methoxysilane, tris(ethylamino)t-butoxysilane, and tris(ethylamino)cyclohexoxysilane.

19. The aminosilane compound according to claim 1, selected from the group consisting of (di-t-butylamino)(ethylamino)diethoxysilane, (cyclopentylamino)(diphenylamino)dimethoxysilane, (benzylamino)(diisopropylamino)diethoxysilane, (di-t-butylamino)(t-butylamino)(ethylamino)methoxysilane, bis(ethylamino)(diethylamino)ethoxysilane, bis(perhydroisoquinolino)(methylamino)methoxysilane, bis(perhydroisoquinolino)(ethylamino)methoxysilane, bis(diethylamino)(ethylamino)methoxysilane, and bis(diethylamino)(ethylamino)n-butoxysilane.

20. The aminosilane compound according to claim 1, selected from the group consisting of bis(ethylamino)(diphenylamino)ethoxysilane, t-butyl(ethylamino)diethoxysilane, cyclohexyl(ethylamino)dimethoxysilane, ethyl(t-butylamino)dimethoxysilane, ethyl(t-butylamino)diethoxysilane, bis(ethylamino)sec-butylmethoxysilane, and bis(ethylamino)cyclopentylmethoxysilane.

* * * * *

UNITED STATES PATENT AND TRADEMARK OFFICE
CERTIFICATE OF CORRECTION

| | |
|---|---|
| PATENT NO. | : 8,247,504 B2 |
| APPLICATION NO. | : 11/997924 |
| DATED | : August 21, 2012 |
| INVENTOR(S) | : Takefumi Yano et al. |

It is certified that error appears in the above-identified patent and that said Letters Patent is hereby corrected as shown below:

On the title page, Item (73), the Assignee's information is incorrect. Item (73) should read:

--(73) Assignee: Toho Titanium Co., Ltd.,
Chigasaki-shi (JP)--

Signed and Sealed this
Second Day of October, 2012

David J. Kappos
*Director of the United States Patent and Trademark Office*